United States Patent
Kiaie et al.

(10) Patent No.: US 8,726,266 B2
(45) Date of Patent: May 13, 2014

(54) METHOD AND SYSTEM FOR UPDATING A MEDICAL DEVICE

(75) Inventors: Namvar Kiaie, Danville, CA (US); Jean-Pierre Cole, Tracy, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 194 days.

(21) Appl. No.: 13/114,020

(22) Filed: May 23, 2011

(65) Prior Publication Data

US 2011/0289497 A1 Nov. 24, 2011

Related U.S. Application Data

(60) Provisional application No. 61/347,813, filed on May 24, 2010.

(51) Int. Cl.
*G06F 9/44* (2006.01)

(52) U.S. Cl.
USPC ........... 717/171; 717/168; 717/174; 717/177; 600/365

(58) Field of Classification Search
USPC ........... 717/168–178; 600/319, 316, 347, 365
See application file for complete search history.

(56) References Cited

U.S. PATENT DOCUMENTS

| | | | | |
|---|---|---|---|---|
| 6,718,547 | B2* | 4/2004 | Takeo | 717/170 |
| 2002/0013613 | A1* | 1/2002 | Haller et al. | 607/60 |
| 2008/0076969 | A1* | 3/2008 | Kraft et al. | 600/300 |
| 2008/0184219 | A1* | 7/2008 | Matsumoto | 717/170 |
| 2009/0204422 | A1* | 8/2009 | James et al. | 705/2 |

OTHER PUBLICATIONS

Chakravorty, Rajiv. "A programmable service architecture for mobile medical care." Pervasive Computing and Communications Workshops, 2006. PerCom Workshops 2006. Fourth Annual IEEE International Conference on. IEEE, 2006, pp. 1-5.*
Bellissimo, Anthony, John Burgess, and Kevin Fu. "Secure software updates: disappointments and new challenges." Proceedings of USENEX Hot Topics in Security (HotSec) (2006), pp. 37-43.*
PCT Application No. PCT/US2011/037624, International Search Report and Written Opinion of the International Searching Authority mailed Sep. 2, 2011.

* cited by examiner

*Primary Examiner* — Satish Rampuria
(74) *Attorney, Agent, or Firm* — Thomas A. Runk; Fulwider Patton LLP

(57) ABSTRACT

Embodiments described herein include methods and/or systems for updating a medical device. Embodiments include medical devices which are configured for updates in response to various events including connection of a peripheral device to the medical device, a user initiated event, or based on received recommendations.

8 Claims, 15 Drawing Sheets

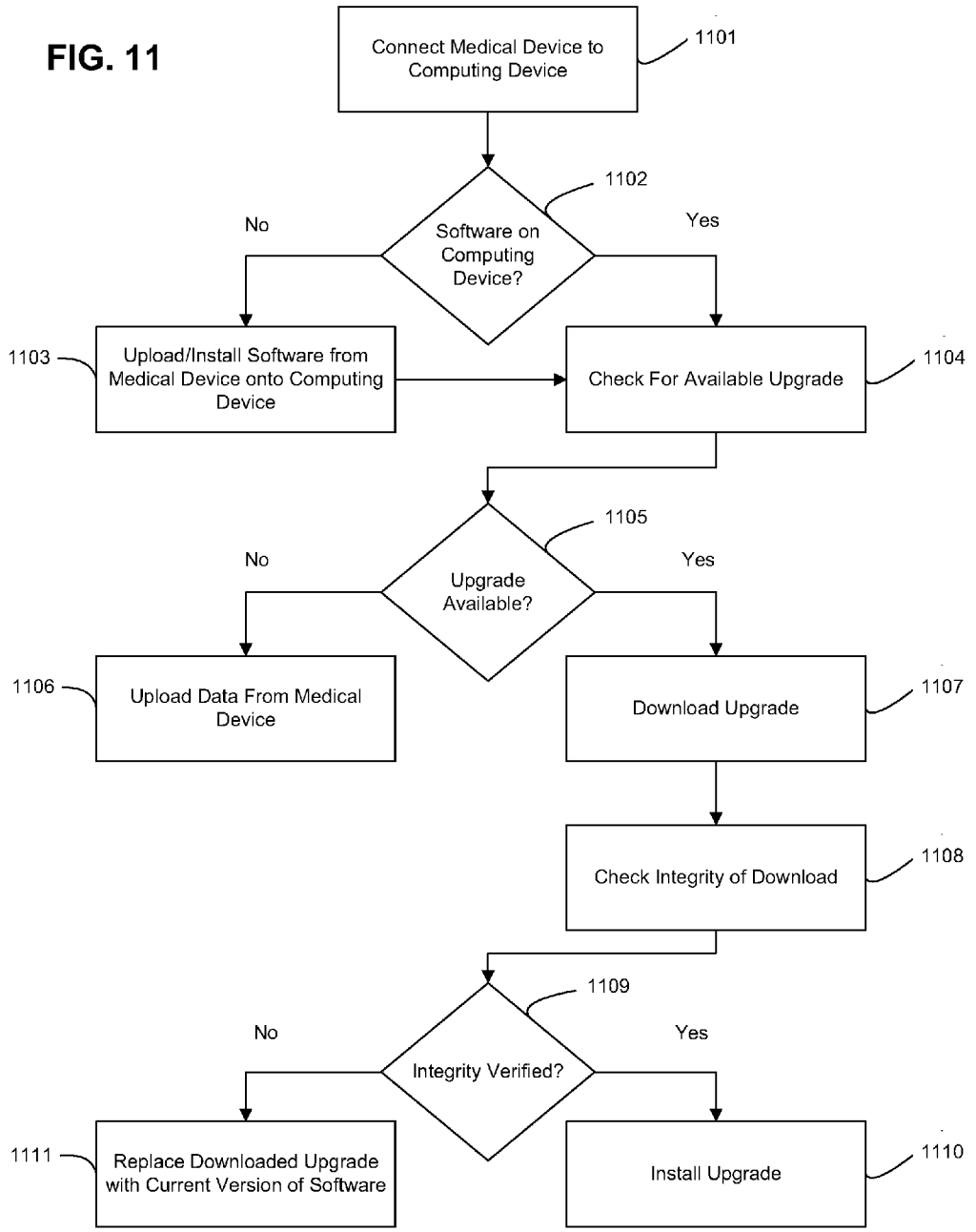

METHOD AND SYSTEM FOR UPDATING A MEDICAL DEVICE

RELATED APPLICATION

The present application claims the benefit of U.S. provisional application no. 61/347,813 filed May 24, 2010, entitled "Method and System for Updating a Medical Device", the disclosure of which is incorporated herein by reference for all purposes.

BACKGROUND

In diabetes management, devices are available for diabetic patients to measure their blood glucose levels. One such type of devices includes blood glucose meters that analyze blood samples via enzyme-based test strips. Typically, the patient lances a finger or alternate body site to obtain a blood sample and applies the drawn blood sample to the test strip in the blood glucose meter housing for analysis and determination of the corresponding blood glucose value which is displayed, stored or otherwise provided to the patient to show the level of glucose at the time of testing. Other commercially available devices include continuous glucose monitoring devices that periodically receive and process analyte related data from a transcutaneous sensor. The received and processed data may then be displayed or otherwise provided to the patient to enable the patient to continuously track measured glucose levels.

With the decreasing cost of electronic components and a corresponding increase in data processing capabilities of microprocessors, computational capability of electronic devices have been rapidly increasing. However, currently available glucose meters are generally configured with limited functionalities related to glucose testing and monitoring.

SUMMARY

Embodiments of the present disclosure include methods and/or systems for updating medical devices. In one embodiment a method for updating a medical device is provided in which a connection between a peripheral device and a medical device is established. In certain embodiments, the peripheral device has at least one functionality not supported or initially included in the medical device. When the peripheral device is identified, data and/or software associated with the peripheral device is also identified. The identified data and/or software corresponds to the at least one functionality not supported or initially included in the medical device. Once the data and/or software is identified, the medical device is updated based on the identified data and/or software and the updated medical device may control the at least one functionality of the peripheral device. In certain embodiments, the medical device includes a blood glucose meter, a continuous glucose monitoring device, an oximeter, a pulse oximeter, a temperature sensor, a respirometer, a heart rate monitor, an electrocardiogram monitor, or a blood pressure monitor.

These and other objects, features and advantages of the present disclosure will become more fully apparent from the following detailed description of the embodiments, the appended claims and the accompanying drawings.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365; 2005/0182306; 2006/0025662; 2006/0091006; 2007/0056858; 2007/0068807; 2007/0095661; 2007/0108048; 2007/0199818; 2007/0227911; 2007/0233013; 2008/0066305; 2008/0081977; 2008/0102441; 2008/0148873; 2008/0161666; 2008/0267823; and 2009/0054748; U.S. patent application Ser. Nos. 11/461,725; 12/131,012; 12/242,823; 12/363,712; 12/495,709; and 12/698,124; 12/714,439; 12/794,721; 12/807,278; 12/842,013; 12/848,075; and 12/871,901 and U.S. Provisional Application Ser. No. 61/347,754.

BRIEF DESCRIPTION OF THE DRAWINGS

FIG. 11 is a flow chart illustrating a method for upgrading software on a medical device and/or a computing device according to embodiments of the present disclosure;

DETAILED DESCRIPTION

Figure 1:
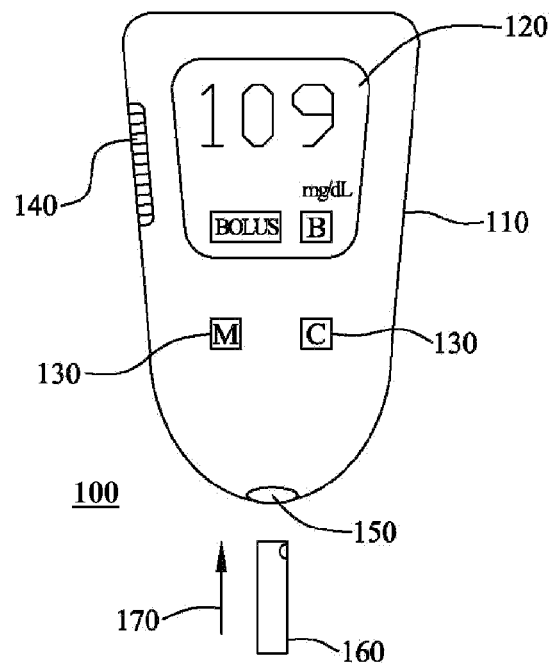
FIG. 1 is a health monitoring device according to embodiments of the present disclosure.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Embodiments described herein relate to upgrading, updating, adding, or modifying a medical device such as, for example a blood glucose monitoring device, a continuous glucose monitoring device, and/or components of an analyte monitoring system. In certain aspects of the present disclosure, the medical device is upgraded and provided with updated software and/or data to assist users in better managing their health. In the manner described, in aspects of the present disclosure, patients with Type-1 or Type-2 diabetic conditions may improve their diabetes management, and further, the patients, users or healthcare providers may be provided with tools to improve the treatment of such conditions.

FIG. 1 shows a health monitoring device 100 in accordance with one embodiment of the present disclosure. Health monitoring device 100 includes a housing 110 with a display unit 120 provided thereon. In certain embodiments, the display unit 120 may be a touch sensitive display. The touch sensitive display is configured to allow a user of the health monitoring device 100 to input data or control operation of the health monitoring device 100. Additionally, the user may adjust various features and/or settings of the health monitoring device 100 using the touch sensitive display.

Also shown in FIG. 1 is a plurality of input buttons 130, each configured to allow the user of the health monitoring device 100 to input or enter data or relevant information associated with the operation of the health monitoring device 100. For example, the user of the health monitoring device 100 may operate the one or more input buttons 130 to enter a calibration code associated with a test strip 160, or other fluid sample reception means, for use in conjunction with the health monitoring device 100. Additionally, the user may operate the one or more input buttons 130 to adjust time and/or date information, as well as other features or settings associated with the operation of the health monitoring device 100. In certain embodiments, the plurality of input buttons 130 are not included on the health monitoring device 100, such as, for example, when the display unit is a touch sensitive display.

In certain embodiments, manual entry of the calibration code associate with the test strip 160 may be unnecessary. Certain embodiments include test strips such as test strip 160 encoded or provided with the associated calibration code, which may be automatically detected and/or processed or retrieved by the health monitoring device 100. In certain embodiments test strips such as test strip 160 may be manufactured such that calibration is unnecessary, obviating the need for the health monitoring device 100 to process, request, or detect such information.

In one embodiment, health monitoring device 100 may include a blood glucose meter with a medication dose calculation function, such as, for example a bolus calculation function configured to calculate a single bolus dosage amount of a medication such as insulin. In certain embodiments, the insulin may be long acting, fast acting or rapid acting insulin.

Health monitoring device 100 may also include an input unit 140 which, in one embodiment, may be configured as a jog dial, or the like, and provided on the housing 110 of the health monitoring device 100. In one embodiment, the user or the patient may operate the input unit 140 to perform calculations and determinations associated with one or more medication dose estimation functions, such as a bolus dose estimation function, of the health monitoring device 100. The input unit 140 may also be used to make or select various options, features, or add-ons that may be available for the health monitoring device 100.

In aspects of the present disclosure, a test strip port 150 may be integrated with the housing of the health monitoring device 100. In certain embodiments, the test strip port 150 is provided in a separate housing or as a separate component that may be physically or electrically coupled to the health monitoring device 100 providing modularity to the health monitoring system. As will be discussed in greater detail below, other components may also be attached to the housing of the health monitoring device 100 to provided added functionality to the health monitoring device 100.

In operation, microprocessor or a control unit 210 (FIG. 2) of the health monitor device 100 may be configured to determine the glucose level in the blood sample, and display the determined glucose level on the display unit 120 when the blood sample is provided on the test strip 160 which is positioned in the strip port 150 of the health monitoring device 100.

In addition to the discrete in vitro glucose testing described above, embodiments include measurement or monitoring of glucose levels and the levels of other analytes, drugs, or physiological conditions based on a user request, prompt or command, or based on a programmed or programmable time schedule (for example but not limited to, such as once every minute, once every five minute, or once every ten minutes). Analyte levels that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. Assays suitable for determining the concentration of DNA and/or RNA are disclosed in U.S. Pat. No. 6,281,006 and U.S. Pat. No. 6,638,716, the disclosures of each of which are incorporated by reference herein. Furthermore, the concentration of drugs, such as, for example, antibiotics (e.g., gentamicin, vancomycin, and the like), digitoxin, digoxin, drugs of abuse, theophylline, and warfarin, may also be determined.

In addition, in accordance with the various embodiments of the present disclosure, the health monitoring device 100 may be configured to automatically enter into a medication dosage calculation mode to, for example, estimate a medication dosage amount based on information stored in the health monitoring device 100 (such as the patient's insulin sensitivity, for example), and/or prompt the patient to provide additional information, such as the amount of carbohydrate to be ingested by the patient for determination of, for example, a carbohydrate bolus dosage determination. The patient may operate the input unit 140 in conjunction with a user interface menu provided on the display unit 120 to provide the appropriate information. Additional features and descriptions of exemplary health monitoring devices including glucose monitoring device and/or blood glucose meters are provided in U.S. patent application Ser. Nos. 12/699,653 filed Feb. 3, 2010 and 12/699,844 filed Feb. 3, 2010, the disclosures of each of which are incorporated in their entirety by reference for all purposes.

In another embodiment, the health monitoring device 100 may be configured to prompt the patient to select whether to retrieve a predetermined or preprogrammed medication dosage amount such as, for example, a correction bolus or a carbohydrate bolus, following the display of the determined analyte level from the test strip 160. In this manner, in one embodiment of the present disclosure, the health monitoring device 100 may be configured to automatically prompt the user or patient to select whether a medication dosage determination is desired following analyte testing using the test strip 160.

Additional information is provided in U.S. Pat. No. 7,041,468 issued on May 9, 2006 entitled "Blood Glucose Tracking Apparatus and Method" and in U.S. Patent Publication No. US2004/0245534 published Dec. 16, 2004 entitled "Glucose Measuring Module and Insulin Pump Combination", the disclosure of each of which is incorporated herein by reference for all purposes.

Figure 2:
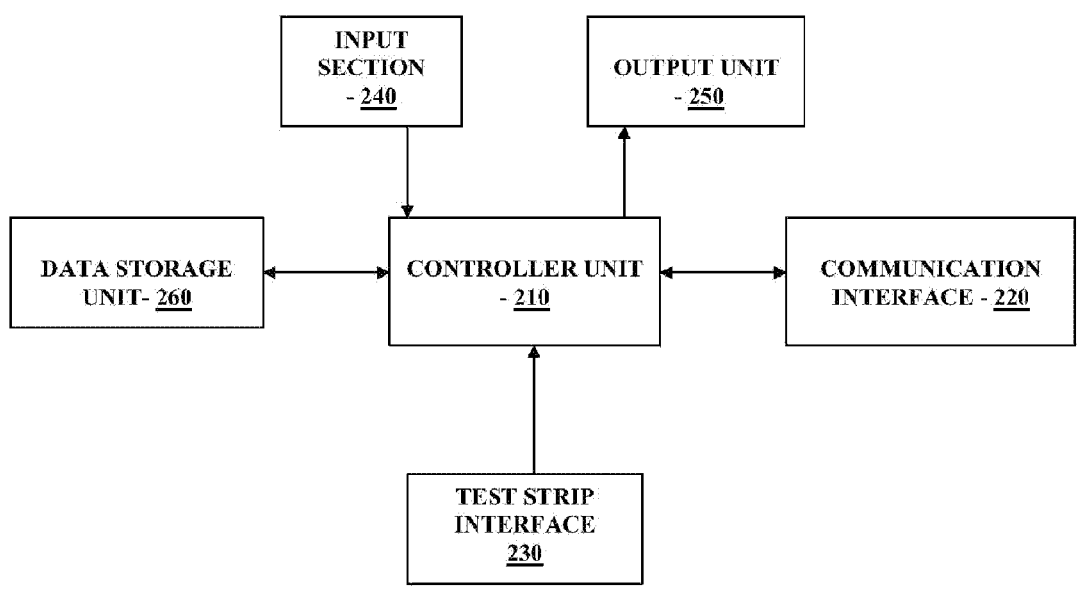
FIG. 2 is a block diagram of the health monitoring device of FIG. 1 according to embodiments of the present disclosure.

FIG. 2 is a block diagram of the health monitoring device 100 (FIG. 1) in one embodiment of the present disclosure. Referring to FIG. 2, the health monitoring device 100 includes a controller unit 210 operatively coupled to a communication interface 220 and configured for bidirectional communication. The controller unit 210 is further operatively coupled to a test strip interface 230, an input section 240 (which, for example, may include the input unit 140 and the plurality of input buttons 130 as shown in FIG. 1), an output unit 250, and a data storage unit 260.

Referring to FIG. 2, in one embodiment of the present disclosure, the test strip interface 230 is configured for signal communication with the inserted test strip 160 (FIG. 1) for determination of the fluid sample on the test strip 160. In addition, the test strip interface 230 may include an illumination segment which may be configured to illuminate the test strip port 150 (FIG. 1) using a light emitting diode (LED), for example, during the test strip insertion process to assist the user in properly and accurately inserting the test strip 160 into the test strip port 150.

Moreover, in a further aspect of the present disclosure, the test strip interface 230 may be additionally configured with a physical latch or other securing mechanism internally provided within the housing 110 of the health monitoring device 100 such that when the test strip 160 is inserted into the strip port 150 the test strip 160 is retained in the received position until the sample analysis is completed. Examples of such physical latch or securing mechanism may include a unidirectional biased anchor mechanism or a pressure application mechanism that retains the test strip 160 in place by applying pressure on one or more surfaces of the test strip 160.

Referring back to FIG. 2, the output unit 250 may be configured to output or display data or information to a user on a display unit, such as display unit 120 (FIG. 1). Such information may include the determined analyte level, software upgrade progress mode and the like. In addition, in still a further aspect of the present disclosure, the output unit 250 and the input section 240 may be integrated, for example, in the case where the display unit 120 is configured as a touch sensitive display where the patient may enter information or commands via the display area using, for example, a finger or stylus or any other suitable input device.

In certain embodiments, the communication interface 220 includes a wireless communication section configured for bi-directional radio frequency (RF) communication with other devices to transmit and/or receive data to and from the health monitoring device 100. In addition, the communication interface 220 may also be configured to include physical ports or interfaces such as one or more of a USB port, an RS-232 port, a serial port, a IEEE 1394 (Firewire) port, an Ethernet port or any other suitable electrical connection port to allow data communication between the health monitoring device 100 and other external devices such as a computer terminal (for example, at a physician's office or in hospital environment), a personal computer, a laptop computer, a notebook computer, an iPad, a tablet computing device, a cellular telephone, a smart phone, a personal data assistant, a workstation, a server, a mainframe computer, a cloud computing system, an external medical device, such as an infusion device, an analyte monitoring device, or including an insulin delivery device, or other devices that are configured for similar complementary data communication.

In other embodiments, the wireless communication section of the communication interface 220 may be configured for infrared communication, Bluetooth communication, wireless USB communication, ZigBee communication, cellular communication, Wi-Fi (IEEE 802.11x) communication, RFID (passive or active) communication, or any other suitable wireless communication mechanism to enable the health monitoring device 100 to communicate with other devices such as infusion devices, analyte monitoring devices, computer terminals, servers, personal computers, laptop computers, notebook computers, iPads, tablet computers, cell phones, smart phones, workstations, mainframe computers, cloud computing systems, communication enabled mobile telephones, personal digital assistants, or any other communication devices with which the patient or user of the health monitoring device 100 may use in conjunction therewith, in managing the treatment of a health condition, such as diabetes.

Figure 3:
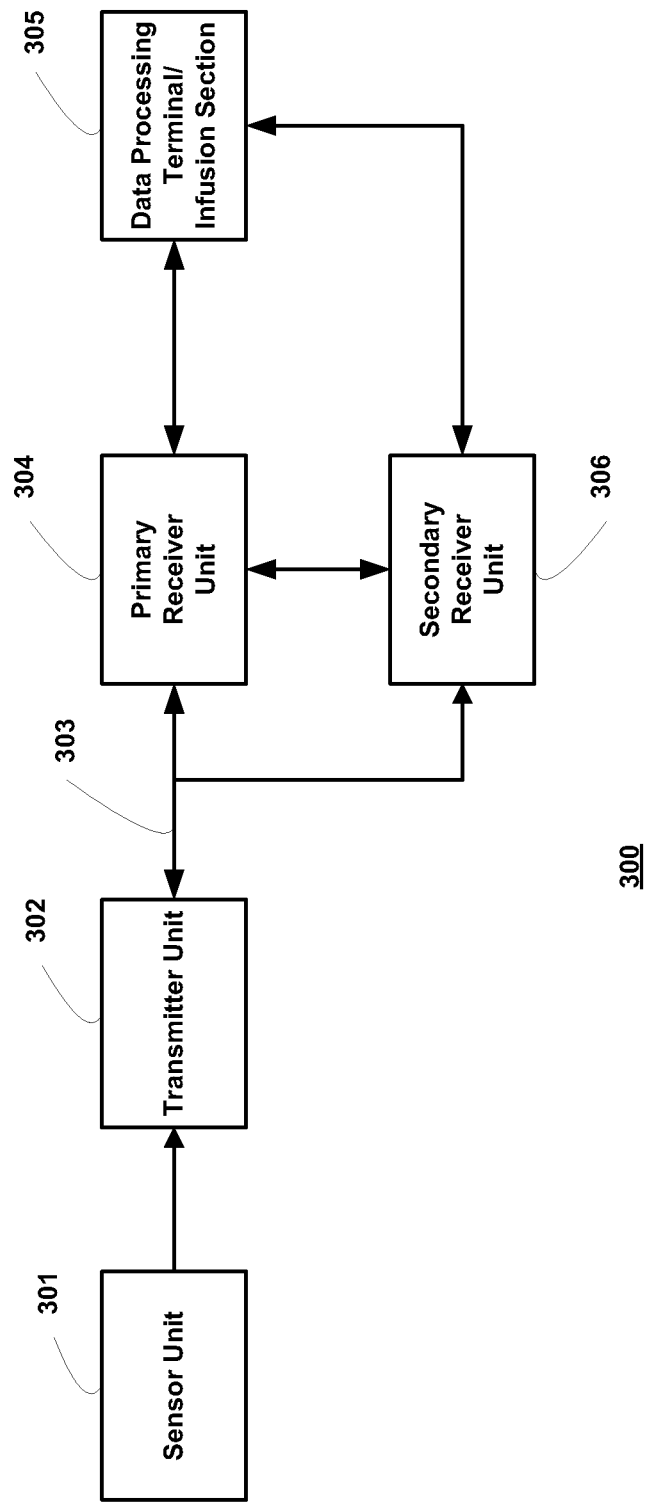
FIG. 3 illustrates a block diagram of a data monitoring and management system according to embodiments of the present disclosure.

Software and firmware upgrades and the methods described herein may also be used with various components of a data monitoring and management system such as the data monitoring and management system 300 illustrated in FIG. 3. In certain embodiments, the system 300 is an analyte monitoring and management system, such as a continuous glucose monitoring management system. Although a continuous glucose monitoring system is specifically mentioned, it is contemplated that features described herein may also be applicable to other medical monitoring device such as drug or medication delivery devices and the like.

Referring back to FIG. 3, the analyte monitoring system 300 includes a sensor 301, a data processing and/or communication unit such as, for example, a transmitter unit 302 coupleable to the sensor 301, and a primary receiver unit 304 which is configured to communicate with the transmitter unit 302 via a bi-directional communication link 303. In certain embodiments, the communication link 303 may include an RF communication protocol, an infrared communication protocol, a Bluetooth enabled communication protocol, a wireless USB communication protocol, a ZigBee communication protocol, a cellular communication protocol, a Wi-Fi (IEEE 802.11x) communication protocol, or an equivalent wireless communication protocol which would allow secure, wireless communication of several units (for example, per HIPPA requirements) while avoiding potential data collision and interference.

Although not shown, it is contemplated that the sensor 301 and the transmitter unit 302 may be configured as a single integrated unit such as an on body patch device. In such embodiments, the integrated unit may wirelessly communicate with other components of the system 300 such as described herein.

The primary receiver unit 304 may be further configured to transmit data to a data processing terminal 305 for evaluating the data received by the primary receiver unit 304. Moreover, the data processing terminal 305 in one embodiment may be configured to receive data directly from the transmitter unit 302 via a communication link which may optionally be configured for bi-directional communication. Accordingly, transmitter unit 302 and/or receiver unit 304 may include a transceiver.

Also shown in FIG. 3 is an optional secondary receiver unit 306 which is operatively coupled to the communication link and configured to receive data transmitted from the transmitter unit 302. Moreover, as shown in the Figure, the secondary receiver unit 306 is configured to communicate with the primary receiver unit 304 as well as the data processing terminal 305. Indeed, the secondary receiver unit 306 may be configured for bidirectional wireless communication with each or one of the transmitter unit 302, the primary receiver unit 304 and the data processing terminal 305. In one embodiment of the present disclosure, the secondary receiver unit 306 may be configured to include a limited number of functions and features as compared with the primary receiver unit 304. As such, the secondary receiver unit 306 may be configured substantially in a smaller compact housing or embodied in a device such as a wrist watch, pager, mobile phone, PDA, for example. In certain embodiments, the secondary receiver unit 306 may be configured with the same or substantially similar functionality as the primary receiver unit 304. Each receiver unit may be configured to be used in conjunction with a docking cradle unit, for example for one or more of the following or other functions: placement by bedside, for recharging, for data management, for night time monitoring, and/or bidirectional communication device.

In one aspect sensor 301 may include two or more sensors, each configured to communicate with the transmitter unit 302. Furthermore, only one transmitter unit 302, communication link 303, and data processing terminal 305 are shown in the embodiment of the monitoring system 300 illustrated in FIG. 3. However, it will be appreciated by one of ordinary skill in the art that the analyte monitoring system 300 may include one or more sensors, multiple transmitter units 302, communication links 303, and data processing terminals 305. Moreover, within the scope of the present disclosure, the analyte monitoring system 300 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 300.

In one embodiment of the present disclosure, the sensor 301 is physically positioned in or on the body of a user whose analyte level is being monitored. The sensor 301 may be configured to continuously sample the analyte level of the user and convert the sampled analyte level into a corresponding data signal for transmission by the transmitter unit 302. In certain embodiments, the transmitter unit 302 may be physically coupled to the sensor 301 so that both devices are integrated in a single housing and positioned on the user's body. The transmitter unit 302 may perform data processing such as filtering and encoding on data signals and/or other functions, each of which corresponds to a sampled analyte level of the user, and in any event transmitter unit 302 transmits analyte information to the primary receiver unit 304 via the communication link 303. Additional detailed description of the continuous analyte monitoring system and its various components are provided in but not limited to: U.S. Pat. Nos. 6,134,461, 6,175,752, 6,121,611, 6,560,471, 6,746,582, and U.S. Patent Publication No. 2008/0278332 filed May 8, 2008 and elsewhere, the disclosure of each of which are incorporated by reference for all purposes.

Figure 4:
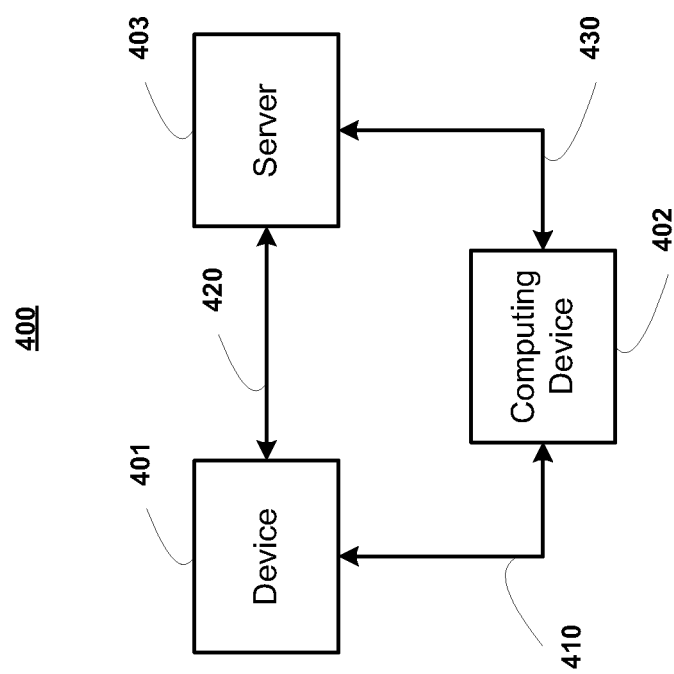
FIG. 4 illustrates a block diagram of an upgrade and recovery system according to embodiments of the present disclosure.

FIG. 4 illustrates a block diagram of an upgrade and recovery system according to embodiments of the present disclosure. In certain embodiments, the system 400 includes, but is not limited to, a device 401, a computing device 402, and a server 403. As will be appreciated by one of ordinary skill in the art, the upgrade recovery system 400 may be used with the health monitoring device 100 (FIG. 1) and components thereof and/or various components of the data monitoring and management system 300 (FIG. 3). As such, as used herein, the term "device", such as device 401 for example, may refer to the health monitoring device 100, the transmitter unit 302, the primary receiver unit 304, and/or the secondary receiver unit 306.

In certain embodiments, the computing device 402 may be a user's personal computer or laptop, for example. The computing device may also correspond to a personal digital assistant, smart phone, cell phone, tablet computer, iPad, or other such portable computing device. The computing device 402 may be configured to store and/or further analyze either user-entered data (such as blood glucose data and/or continuously monitored glucose data) measured from the device 401 or data that was transmitted to the device 401 via a wireless or wired connection. In certain embodiments, web-based application software and other client software may be stored in memory of the computing device 402 and may be executed by one or more processors of the computing device 402. Such software may enable a user to view analyte related data, available software and firmware upgrades for the device 401, as well as various available applications for the device 401.

In certain embodiments, server 403 is configured to provide upgrades for the device 401 and/or the computing device 402. The upgrades to the device 401 and the computing device 402 include software upgrades, data upgrades, and firmware upgrades. The server 403 is further configured to store and/or analyze and process data obtained from device 401 and computing device 402 and transmit the received data to another computing device (not shown) such as, for example, a computing device of a healthcare provider. Other external components and/or devices (not shown) may be connected to server 203. Additional description for exemplary upgrade and/or recovery systems, such as the system 400 of FIG. 4, are provided in, for example, U.S. provisional application No. 61/184,234, entitled "Failure Recovery Methods of Corrupted Device Or During Software Downloads and Preservation of User Data and Manufacturing Data", filed on Jun. 4, 2009, the disclosure of which is incorporated herein by reference in its entirety for all purposes.

In certain embodiments, communication links 410, 420, and 430 may respectively connect the device 401 and computing device 402; device 401 and server 403; and computing device 402 and server 403. The communication links 410, 420, and 430 may include one or more of an RF communication protocol, an infrared communication protocol, a Bluetooth enabled communication protocol, a Wireless USB communication protocol, a ZigBee communication protocol, a cellular communication protocol, a Wi-Fi (IEEE 802.11x) communication protocol, an equivalent wireless communication protocol, and the like.

One or more components of the upgrade and recovery system 400 may function to perform various and multiple upgrade and recovery operations related to software and data upgrades, recovery, and/or preservation. In certain embodiments, system 400 may perform one or more routines for downloading data and/or software to a device, such as device 401 as described below in conjunction with the flowchart of FIG. 5.

Figure 5:
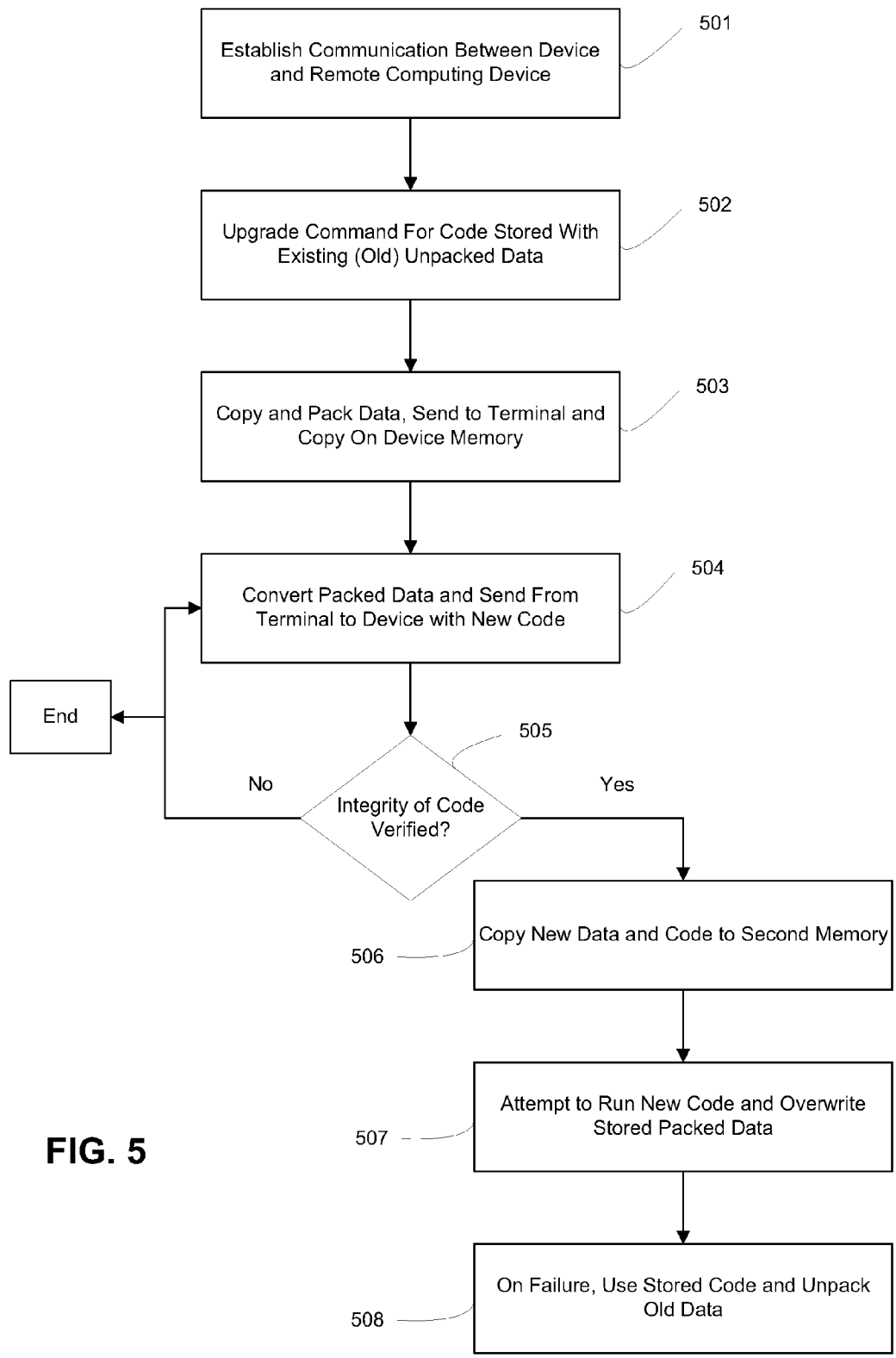
FIG. 5 is a flowchart illustrating a method for updating a medical device according to embodiments of the present disclosure.

Referring to FIG. 5, communication between a medical device, such as device 401 (FIG. 4), and at least one remote computing device, such as computing device 402 or server 403, is established (501). In certain embodiments, communication is established through communication links 410 or 420.

In one aspect, the device 401 includes a first memory for storing data and/or software algorithm or routines for execution by one or more microprocessors to upgrade executable code for operation of the device 401 and to verify the integrity of the code and/or associated user-configurable and manufacturing data (adapted to be used by the upgraded code). The device 401 further includes a second memory with a multiplicity of segregated areas for storage of different kinds of data and/or software. In one embodiment, the first and/or second memory is random access memory. In other embodiments, the first memory is volatile memory. In yet another embodiment, the second memory is non-volatile memory, which may be flash memory. In certain embodiments, the first memory and the second memory are non-volatile memory. Executable code that is being executed on the device 401, as well as the user-configurable and manufacturing data utilized by the executable code, is stored in a first storage area of the second memory.

Referring still to FIG. 5, in certain embodiments, the device 401 (FIG. 4) receives a command regarding the download of new executable code that is to be processed or executed at the device 401 (502). The new code may be for an upgrade to software being executed on the device 401, a new application programming interface (API) for the device 401, updated firmware for the device 401, or a new software application for the device 401. The upgrade command is initiated by the remote computing device 402 and communicated by the remote computing device 402 to the device 401. In certain embodiments, a processor of the device 401 automatically initiates installation or downloading of the new code directly from the server 403 when it is determined an upgrade is available. In other embodiments, the download will not be initiated until a user confirms that the available upgrade is desired.

When the download is initiated, the existing (old) unpacked user-configurable data and manufacturing data utilized in the current software version running on the device (stored in a first memory area of the second memory) is packed and copied with the current executable code to a second storage area of the second memory of the device 401 (503). This data may then be uploaded to the computing device 402 running the software upgrade module or may be uploaded directly to the server 403.

The uploaded old packed data is converted to be utilized by the new (upgraded) version of the software code. Once converted, the new software code is downloaded to the device 401 as new (converted) data with a new version of the code and is stored in the first memory of the device 401 (504). The server 403 may, according to an embodiment, perform the upload and download through client software running on the server 403, an intervening device, such as, for example, the computing device 402, or directly on the device 401.

The integrity of the new converted data block and upgraded code stored on the first memory of the device is verified (505). The verification may include confirmation that the new data and code are not corrupt or that the new data and code are compliant with device 401. The integrity verification is, according to an embodiment, performed by cyclic redundancy check (CRC). Although a cyclic redundancy check is specifically mentioned, it is contemplated that other integrity verification processes including error detection and/or correction may be employed to verify the new data and code.

If the verification of the new data and code is satisfactory, the new (converted) packed data and original software code are copied to a third storage area of the second memory of the device 401 (506). As the new (converted) packed data is stored in the third storage area, the packed data and code that is stored in the second storage area of the second memory of the device 401 is overwritten with the verified new data and code.

If the verification of the new data and/or code is unsatisfactory, due to corrupt data or data noncompliance, for example, the process may end. In certain embodiments, the new data and/or code, if corrupt, is neither stored in the first nor second memory. The process may then repeat where new (converted) data and upgrade code are again downloaded to the device 401 as described above.

When the download and copying are complete, in certain embodiments, a processor of the device 401 initiates a reset command to reset the device 401. Once the reset is complete, the device 401 attempts to use the newly upgraded code and the new data (507). As the device is attempting to use the newly upgraded code, the packed (verified and converted) data that is stored in the second area of the second memory is unpacked to populate the first area of the second memory. If a failure occurs, the process stops and the processor of the device 401 initiates a reset command (508). Upon recovery of the reset, the device 401 reverts to use of the old (unconverted) data and original (not yet upgraded) code that was stored in the second storage area of the second memory.

In certain embodiments, the upgraded code may be associated with a critical update for the operation or functionality of the device 401 (FIG. 4). In certain aspects, if the critical update is not installed on the device 401, the device 401 may not function properly. For example, the critical update may correspond to a bolus calculation function or bolus delivery function of peripheral pump connected to the device 401. If the critical update is not installed on the device 401, an incorrect bolus dosage may be calculated and/or the pump may not deliver the expected amount of insulin based on the calculation.

In certain aspects, if a failure occurs during the installation of the critical update on the device 401, the processor of the device 401 initiates a reset command and the device 401 resets. When the device 401 recovers from the reset, the download and/or installation of the critical update automatically restarts. In certain embodiments, when the device 401 recovers from the reset, the user of the device 401 may be prompted to reinitiate the download and/or installation of the critical update. The prompt may be a message screen output on a display of the device 401, an audible alert, a tactile alert or a combination thereof.

In certain embodiments, when the device 401 recovers from the reset, the device reverts to the use of the old data and original code that was stored in the second storage area of the second memory but the functionality or feature of the device 401 that corresponds to the critical update will not be accessible by the user until the critical update is installed. For example, if the critical update corresponds to a bolus calculation function, the user may not use the bolus calculation function until the critical update corresponding to the bolus calculation function is installed on the device 401. Although the bolus calculation function is not operational, other features and functionalities of the device 401 may still be functional. For example, although a bolus calculation function is not accessible by the user, a test strip port and blood glucose calculation function may be operational on the device 401.

It is also contemplated that although the critical update may correspond to a particular feature of the device 401, all functionalities and features of the device 401 may be non-functional. In such cases, a message or alert screen may be output on the display of the device 401 indicating that all features and functionalities of the device 401 are non-functional and will remain non-functional until the critical update has been installed on the device 401. The user may then be prompted to reinitiate the download and/or installation of the critical update.

In yet another aspect, the functionality of the device 401 that corresponds to the critical update may have limited operational capabilities for a predetermined amount of time. For example, if the critical update corresponds to medication delivery of the peripheral pump, the processor of the device may instruct the peripheral pump to deliver a predetermined amount of insulin for the predetermined amount of time. When the predetermined amount of time expires, the user may be prompted to reinitiate the download and/or installation of the critical update.

In certain embodiments, the first memory of the device 401 also includes non-user configurable data. Such non-configurable data includes, for example, manufacturing data (e.g., circuit calibration information) that enhances or assists in the operation of the device 401. Thus, it may be necessary or beneficial to receive updated or new non-user configurable data. For example, the updates or new data may be necessary for the code upgrade.

In certain embodiments, the non-user configurable data may be used to identify the device 401 such as, for example, with a device serial number. Additionally, the non-user configurable data may also include default settings for the device 401 or a current software version of the device 401. It may be desirable to keep the default settings of the device 401 intact in case the downloading of new non-user configurable data fails or previously-used non-user configurable data has operational problems. Because the non-user configurable data is stored, this data may be used to restore the settings of the device 401 should any problems occur. In certain embodiments, the restoration of the default settings may occur automatically upon receipt of the non-user configurable data or upon a user-initiated or remote-initiated command.

Figure 6:
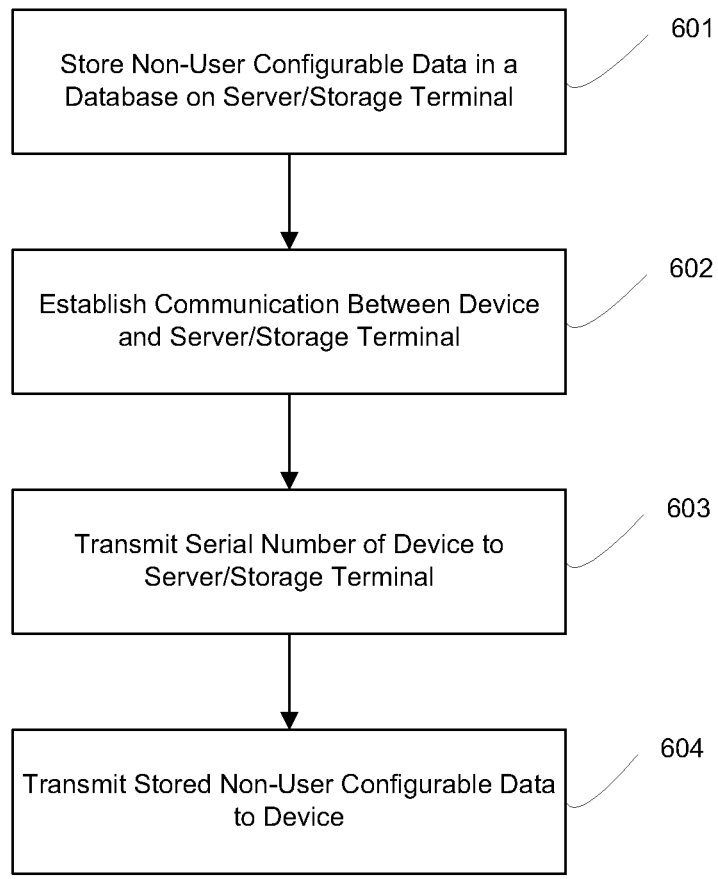
FIG. 6 is a flowchart illustrating a method for recovering non-user configurable data according to embodiments of the present disclosure.

FIG. 6 is a flow chart illustrating a method for use in one or more embodiments of the present disclosure, for recovering non-user configurable data used by a device, such as, for example device 401 (FIG. 4), in which such data has been corrupted or is no longer present. Referring to FIG. 6, the non-user configurable data, which is specific to the device 401, is stored in a database on a remote server, data storage terminal, or other computing device (601). As discussed above, the non-user configurable data may be manufacturing-configured data that assists in or supplements the operation of the analyte monitoring device. In other embodiments, the non-user configurable data is associated with a serial number that identifies the device 401, a current software version running on the device 401 and/or default settings of the device 401.

Still referring to FIG. 6, electronic data communication between the remote server, the data storage terminal or the computing device and the device 401 is established (602) and the serial number for the device 401 is transmitted to the server, the data storage terminal or the computing device (603). Such transmission may be initiated by a user of the device 401 upon experiencing, for example, a malfunction or problem with the device 401. The user may provide the serial number through a user interface of the device or through a user interface on a device that is in communication with the device 401. In certain embodiments, the device 401 automatically transmits the serial number based on various performance indicators such as, for example, when a failure of the device 401 is detected.

Upon receipt of the serial number, the remote server, the data storage terminal, or the remote computing device transmits the stored non-user configurable data to the device 401 (604). The transmission of the data may be automatically performed upon receipt of the serial number, as a receipt of the serial number may indicate that the device 401 requires the data. In certain embodiments, transmission of the stored non-user configurable data may be transmitted only when the serial number is received with an appropriate request to transmit the data.

As previously discussed, the non-user configurable data may identify the device 401 and may include default settings for the device 401, including the most recent software and firmware versions that were running on the device 401. When the default settings are received, the device 401 may use the default settings to restore the device to its functionality prior to any operational problems that may have occurred. In certain embodiments, transmission of the stored non-user configurable data to the device 401 from the server, the data storage terminal or the computing device may cause the default settings to be automatically restored on the device 401. The restoration of the default settings may be processed by the remote server, the data storage terminal, or other computing device through a corresponding tool or software component running on the corresponding device.

Figure 7:
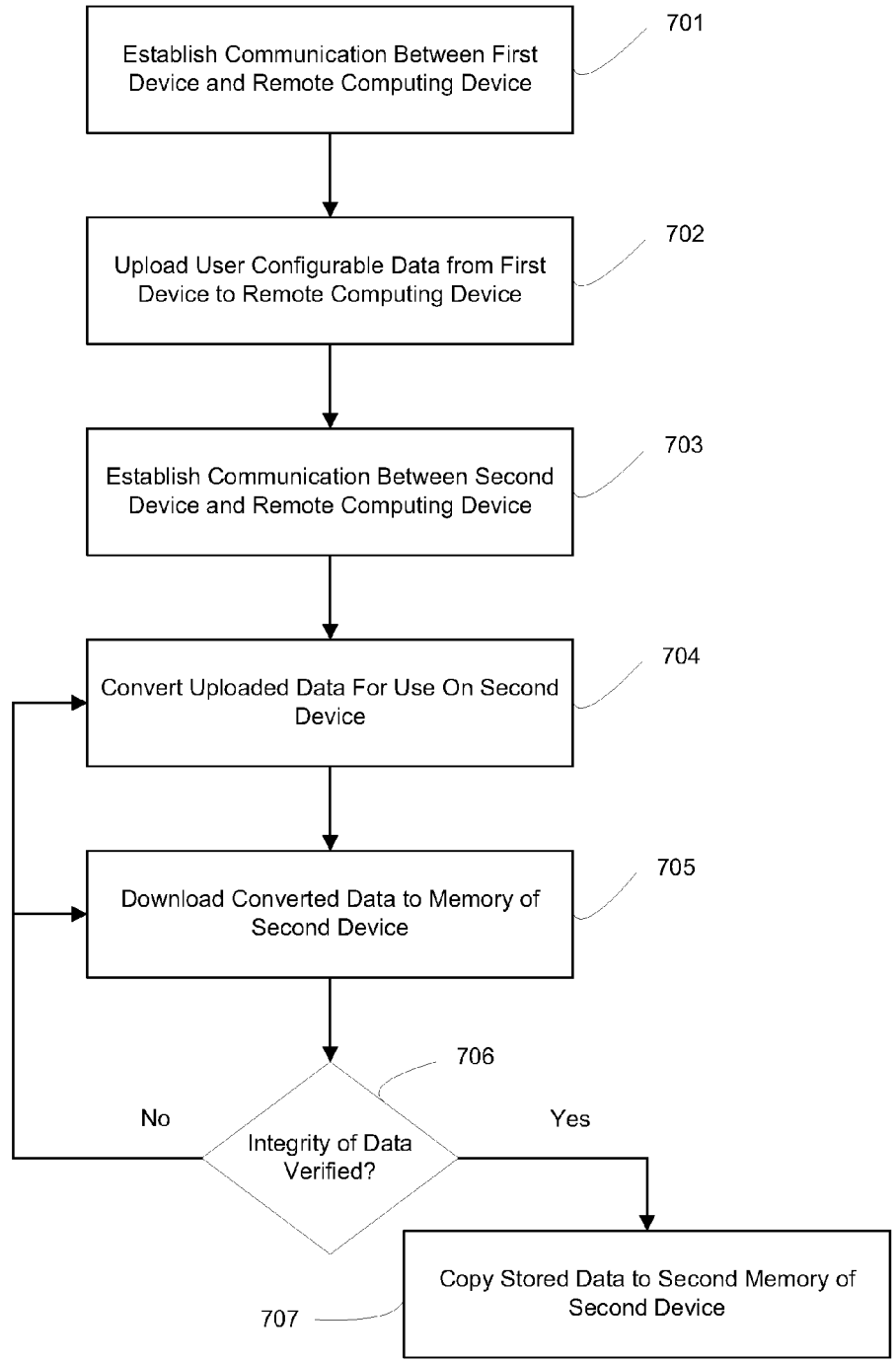
FIG. 7 is a flowchart illustrating a method for transferring user configurable data from a first device to a second device according to embodiments of the present disclosure.

FIG. 7 illustrates a routine for transferring user configurable data from a first device to a second device according to embodiments of the present disclosure. The routine described herein may be used when the first device ceases to work or use of another device is desired (e.g., when a physician prescribes use of a different device). The method routine described below may also be used to transfer applications and other downloaded content from one device to another. In certain embodiments, the method may be used to transfer data from the first device to the second device even if the devices are not related or serve different functions.

Referring to FIG. 7, electronic data communication is established between the first device and a remote computing device (701). In certain embodiments, the connection may be a wired or wireless connection such as described above. In further embodiments, when the communication link is established, the first device may send an identifier, such as, for example a serial number to identify the type of the first device and/or a current software version being executed on the device. This data may be sent automatically or in response to a request from the remote computing device. When the first device has been identified, user configurable data is uploaded from the first device to the remote computing device (702). In certain embodiments, the remote computing device is a server. In other embodiments, the remote computing device may be a personal computer, laptop, personal digital assistant, smart phone, tablet computer, or other such computing device.

The specific data that is uploaded may be dictated by either the first device or the remote computing device. For example, if some of the data to be uploaded was recently uploaded in the past and the data has not been changed, the data need not be uploaded again as it is duplicate data. In certain embodiments, if some of the data to be uploaded was received and/or stored on the device prior to a threshold time limit (e.g., 6 months in the past) the data may no longer be needed. Further, data transferred from one device may not be compatible with the second device. In such cases, the unneeded data will not be uploaded to the remote computing device.

Still referring to FIG. 7, once the data from the first device has been uploaded to the remote computing device, electronic data communication is established between the second device and the remote computing device (703). As discussed above, the electronic data communication may be a wired or wireless connection. Further, the established communication between the second analyte monitoring device and the remote server need not be direct but may be routed through other servers and/or various devices. In certain embodiments, when a connection is established between the second device and the remote computing device, the second device may send either automatically, or in response to a request from the remote computing device, an identifier that may be used to identify the device and/or a current software version running on the device. When the second device has been identified, the data that was uploaded from the first device is converted for use on the second analyte monitoring device (704).

When the data has been converted, the converted data is downloaded and stored on the second device (705). In certain embodiments, the downloaded data is stored in a first memory of the second device. In certain embodiments, the download operation may be performed by a software upgrade tool running on a computing device connected to the second device. In certain embodiments, the remote computing device performs the download through client software running on a computing device that connects to the second device. In other embodiments, the software upgrade tool may be incorporated directly into the second device.

Referring back to FIG. 7, once the data has been stored on the second device, the integrity of the stored data is verified (706). The verification may serve to confirm that the stored data is not corrupted or that if the data was converted, the data is compliant with the second device. In certain embodiments, the integrity verification may be performed by cyclic redundancy check (CRC) or other integrity verification processes.

In certain embodiments, when the data stored on second device has been verified, a copy of the data is stored on a second memory of the second memory device (707). In certain embodiments, the remote computing device may direct a computing device connected to the second device to perform the copying operation through client software running on the connected computing device. In other embodiments, the data copying may be performed on the second device itself without the need for further instructions from another computing device. When the data has been transferred to the second memory of the second device, the second device may operate based on the stored data. In certain embodiments, the second device continues to operate based on its previously-stored data until further operations/instructions are performed in which the new data is needed.

If it is determined that the converted, stored data has not been verified (706), the method returns to 704 or 705 to convert the uploaded data or to download the converted data, respectively, as one of these operations may have initially failed or been processed incorrectly. According to the above-described embodiments, a user is advantageously able to recover device functionality from a server or another location rather than replace the device, and the recovery may conveniently be done from the user's home or other preferred location. Thus, installation of corrupted software, through, for example, a software upgrade tool running on a user's computing device, may conveniently be resolved.

Moreover, during a software upgrade of a medical device, several points of failure exist that are recovered by the medical device and/or a software tool operating on a user's computing device. The recovery by the medical device and/or software tool serves to consistently provide the user with a functioning device even if the software upgrade is unsuccessful. The points of failure may include, but are not limited to, (i) corruption of the software upgrade during download or upon restarting of the medical device; (ii) data that is corrupt or inconsistent with the new software upgrade; (iii) communication failure between the computing device and the device or the server during the software upgrade process; and (iv) device automatic recovery from incorrect software or data.

To solve and/or alleviate the points of failure, the device may operate to correct its software, manufacturing data, and any user configured data by using the saved version of the software and the data. Thus, the communication link between the computing device and the device, as well as the communication link between the computing device and the server, is not necessary for the device to remain functional. Additionally, the user of the device is able to perform software upgrades without relying on a software manufacturer or other professional.

During a software upgrade on a device, it is important that user-configured data as well as manufacturing-configured data is not lost or corrupted. In certain embodiments, to protect the data, a software upgrade tool running on the user's computing device obtains the current data for the current release of the software at the start of the software upgrade process. Before the new software upgrade is initiated on the device, converted user-configured and manufacturing-configured data that is compliant with the new software is downloaded. The server performs the software upgrade as well as the data conversion to match the new software through client software running on the user's computing device that connects to the user's device. The user of the device is able to perform software upgrades while the user-configured and manufacturing-configured data are preserved. Moreover, the data is converted and used with the new software release.

For a software upgrade on a device, data is secured and/or preserved. Accordingly, the data is copied to a block and is later restored to the device. This operation reduces interaction between the device and computing device, thereby reducing the likelihood of point-of-communication failure, and also allows for a user to easily perform software upgrades on the device. Additionally, a hospital or clinic can perform software upgrades or upload user data from one device and download it to another device.

Figure 8:
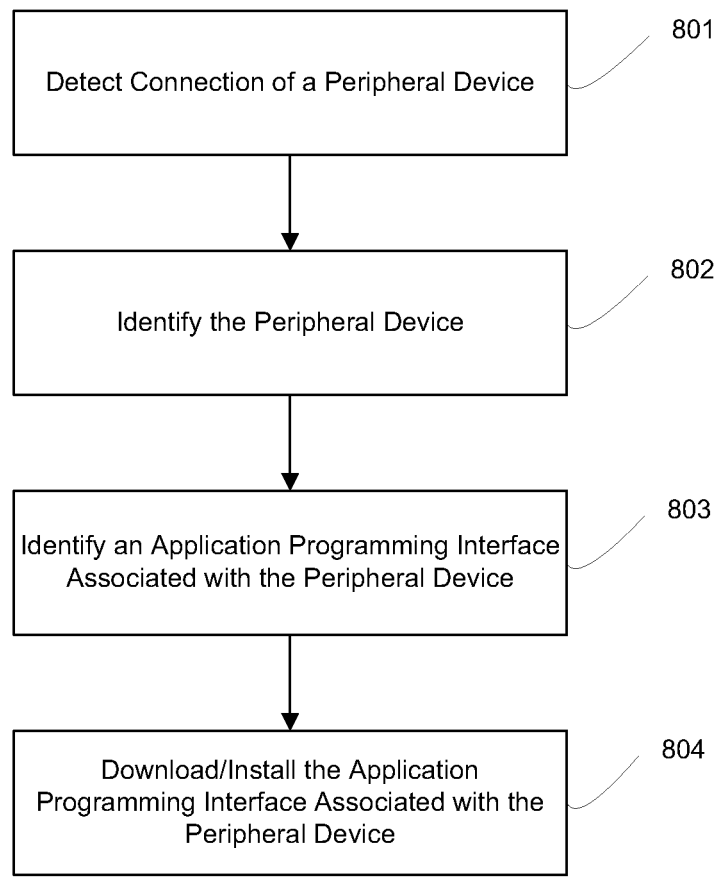
FIG. 8 is a flow chart illustrating a method for upgrading a medical device based on detecting a connection with a peripheral device according to embodiments of the present disclosure.

FIG. 8 illustrates a routine for upgrading a medical device based on detecting a connection with a peripheral device according to embodiments of the present disclosure. In certain embodiments, the routine described below may be used with a medical device, such as, for example, a health monitoring device 100 (FIG. 1), a primary receiver unit 304 (FIG. 3) or secondary receiver unit 306 (FIG. 3).

Referring to the Figure, when a peripheral device is connected to, and detected by, the medical device (801), the identity of the peripheral device is determined (802). In certain embodiments, the peripheral device is a device having functionality that was not, or is not, currently provided on the medical device. For example, if the medical device does not have a test strip port, a peripheral test strip port may be connected to the medical device. Thereafter, as test strips are inserted into the peripheral test strip port connected to the medical device for analyzing blood samples, the medical device may be configured to analyze, display and store data corresponding to blood glucose levels of the blood sample. In another example, the peripheral device may be a pump for delivering a medication, such as, for example insulin. Once the pump for delivering the medication is connected to the medical device, data regarding the medication, such as, for example, medication administered, the type of medication administered, etc., may be stored and/or displayed on the medical device. Although a test strip port and a pump for delivering a medication are specifically mentioned, it is contemplated that various other peripheral devices may be used in conjunction with the medical device. For example, and as will be explained in greater detail below, a peripheral device may be personal digital assistant, cellular telephone, tablet computer or other such device.

In certain embodiments, the peripheral device is physically connected to the medical device. Examples include connecting the peripheral device to a USB port of the medical device either directly or indirectly using a USB cable. Within the scope of the present disclosure, other physical connections may be employed or used such as, for example, but not limited to RS-232 connection, serial data connection, IEEE 1394 data connection, Ethernet data connection, or one or more combinations thereof. In other embodiments, the connection between the peripheral device and the medical device may be made using an RF communication protocol, RFID communication protocol, an infrared communication protocol, a Bluetooth enabled communication protocol, an IEEE 802.11x (WiFi) wireless communication protocol, wireless USB communication protocol, cellular communication protocol, Zigbee communication protocol, or an equivalent wireless communication protocol.

When a wireless connection protocol is used, a user of the medical device may need to prompt the medical device to search for and detect a specific peripheral device from a predetermined or pre-populated list of peripheral devices supported by the medical device. Once a particular peripheral device has been selected by the user using for example a user interface, the medical device may require that the peripheral device be brought within a predetermined range of the medical device. When the peripheral device is brought within the predetermined range, a communication link may be established between the two devices. In yet another embodiment, the user may manually enter an identification number or serial number of a particular peripheral device into the medical device and when a peripheral device having that serial number is within a certain predetermined range, the communication link is established. In certain embodiments, the medical device may be configured to only attempt to connect to peripheral devices that come within a predetermined range of the medical device (e.g. 3 feet or less, 2 feet or less, etc.). As a result, the medical device will not attempt to connect to peripheral devices that are not owned by the user or attempt to connect to a peripheral device that the user did not intend to be connected to the medical device.

Referring back to the Figures, when the medical device has detected a connection to the peripheral device, the connected peripheral device is identified (802) using a serial number or other such identifier. As discussed above, the peripheral device may be physically connected to medical device, such as, for example, being connected directly to a USB port on the medical device or connected via a USB cable. In certain embodiments, the peripheral device may be wirelessly connected to the medical device. When the connection is established, the peripheral device is identified using a serial number of the device, a portion of the serial number of the device or other such identifier that may distinguish the peripheral device from another peripheral device. In certain embodiments, and as discussed above, the peripheral device is identified by a user prior to a connection being established.

When the serial number or other identifier is received, a processor of the medical device compares the received serial number of the peripheral device, or portions thereof, to a database of supported peripheral devices stored in a memory the medical device to properly identify the connected peripheral device. The peripheral device is identified when the serial number or identification number of the peripheral device matches a serial number or identification number of a type of peripheral device stored in the database. In certain embodiments, the medical device is configured to wirelessly connect to a remote computing device such as for example, a server, and request identification of the peripheral device based on the received identification number or serial number.

In certain embodiments, the peripheral device may be selected from a user interface of data management software being executed on a computing device and configured to interact with the medical device. As will be described in greater detail below, the data management software may be used to receive data from the medical device, print various reports based on the received data, and share the received data with healthcare providers or other caretakers over a network connection. In certain embodiments, when the medical device is connected to the computing device on which the data management software is being executed, a user may manually select a peripheral device from a list of available or supported peripheral devices on a user interface screen of the data management software and request that the medical device be upgraded to support the selected peripheral device.

Referring back to FIG. 8, when the peripheral device has been identified, an application programming interface (API) associated with the identified peripheral device is also identified (803). An application programming interface enables the medical device to interact with software of the peripheral device. For example, if the peripheral device is a pump for dispensing medication, installation of the API on the medical device may permit the medical device to act as a pump controller to control medication delivery, calculate amounts of medication to be delivered, and receive and display data corresponding to the medication delivered by the pump. In certain embodiments, the API is identified based at least in part, on the serial number or identification number of the peripheral device that was connected to the medical device. In certain embodiments, a user may select a particular API from a pre-populated list of available APIs, such as, for example, a list of APIs on a user interface screen of the data management software.

Once the appropriate API has been identified, the API is downloaded and installed on the medical device (804). In certain embodiments, the peripheral device API may be stored or located on a computer, server, and/or network located external to medical device. As such, the medical device may connect to the computer or server on which the identified API is stored to download the identified API. In certain embodiments, the software for the identified API may reside, for example, in a memory of the medical device. Thus, when the peripheral device is connected to the medical device and identified, a processor of the medical device automatically, or based on user verification, retrieves the identified API from memory and install the identified API software. In yet another embodiment, the API software for the peripheral device may reside in a memory of the peripheral device. Thus, when the connection between the peripheral device and the medical device is established, a processor of the medical device may issue a command to download and install the data and/or software from the peripheral device thus enabling the medical device to communicate with and/or control the peripheral device.

In certain embodiments, the peripheral device is configured to reprogram or update the medical device such that the medical device can communicate with the peripheral device. For example, when a peripheral device is connected to the medical device for the first time and the medical device detects the connection, a processor of the medical device issues a command to download and install the data and/or software stored on the peripheral device to the medical device.

In certain embodiments the peripheral device is a non-medical peripheral device, such as, for example a cellular telephone, personal digital assistant, tablet computer and the like. In such embodiments, the medical device may download and use APIs for the non-medical peripheral devices in the same manner as discussed above. Once the API is installed, the medical device is configured to transmit data, such as, for example, blood glucose readings, to the identified peripheral device and a processor of the medical device instructs the peripheral device to transmit the data to healthcare provider. For example, if the peripheral device is a cellular telephone or personal digital assistant, the medical device, can instruct the cellular telephone to send a SMS message or MMS message to the user's healthcare provider with the blood glucose data or other such data contained in the body of the message.

As will be appreciated by one of ordinary skill in the art, in some embodiments, the API may be downloaded and installed on the medical device in accordance with the method described above with reference to FIG. 5. Further, it is contemplated that the upgrades and downloads will not substantially affect the functionality and performance of the medical device while the user is actually using the medical device to test blood glucose values and view glucose related data. In certain embodiments, if a user is currently using the medical device, such as, for example, performing a blood glucose test, or continuous glucose data is being received at a receiver unit, downloading and/or installation of the upgrade or software is suspended until the user imitated action is complete.

Figure 9:
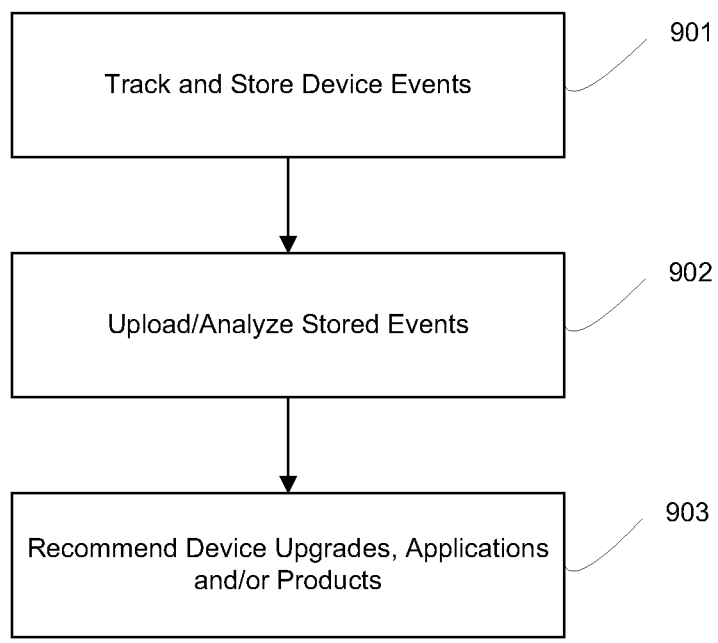
FIG. 9 is a flow chart illustrating a method for updating a medical device according to embodiments of the present disclosure.

FIG. 9 is a flow chart illustrating a method for updating a medical device according to embodiments of the present disclosure. In certain embodiments, the medical device is a health monitoring device 100 (FIG. 1), a primary receiver unit 304 (FIG. 3) or a secondary receiver unit 306 (FIG. 3). The method for updating the medical device begins as various events are detected by a processor of the medical device. Each of the events are then stored and tracked in a device history log (901) that is stored in a memory of the medical device. In certain embodiments, the device history log stored on the medical device is associated with the identification number that corresponds to the medical device.

In certain embodiments, the device history log is configured to track data corresponding to the treatment of a health condition of a user such as, for example, diabetes. Such data may include the frequency of insulin doses, the type and brand of insulin used, the manufacturer of the insulin, frequency of blood glucose measurements, type of test strips used in blood glucose measurements, alarms and alerts output by the medical device and other data related to the treatment of diabetes.

In certain embodiments, the device history log also tracks updates to the firmware and/or software of the medication device as well as current versions of the firmware and/or software being executed on the medical device. Each time the medical device is altered or updated (e.g., new firmware version, software version, peripheral device connection, etc.), the update information is stored in the device history log of the medical device. The modifications to the device, which may include a portion of or all of the modifications to the device, may then be transmitted to a device history record (DHR) stored at a remote location, such as, for example, on a server or other remote location such as device manufacturing site or at a server of a device manufacturing site, accessible via a network. In certain embodiments, server may contain device history logs of multiple devices. Thus, each record or device history log in the device history record has a unique identifier that corresponds to a particular medical device (e.g., identification number of the medical device). Therefore, when data from a particular device history log associated with a medical device is transmitted to the location where the device history record is maintained, the data from the medical device is stored or updated in the device history recorded corresponding to the identified medical device.

The transmission of data from the device history log of the corresponding device to the location where the device history record is maintained may occur directly from the medical device using a wireless or wired communication protocol to connect to the internet or other data network. In certain embodiments, the data from the device history log is transmitted to the device history record location when the medical device is connected to a computing device capable of connecting to a network or the internet. When the connection is established, the device history log for that particular device, identified by the serial number or partial serial number of the device, is updated in the device history record to reflect the changes made to the medical device. Thus, a manufacturer of the device, a healthcare provider or other entity may be able to track the most recent updates to each device. In certain embodiments, the device history records includes the date of manufacture of the associated device, the quantity of manufacture of the associated device, the quantity of the manufactured device released for distribution, acceptance records including indications that the devices are manufactured in compliance with the device master record (DMR) associated with the manufactured device (e.g., medical device), identification label and labeling used for each production unit associated with the device, and/or associated device identification and control number.

In certain embodiments, the information in the device history record is used to assist a user in reverting to a previous version of software should problems arise when upgrading the medical device and/or the computing device. Because data in the device history log is uploaded and stored in the device history record, in certain embodiments, an upgrade to the medical device may only occur when a connection to a network has been established either through the medical device being connected to a computing device having a network connection or when the medical device is directly connected to a network.

In certain embodiments, the device history log is also configured to track occurrences of data synchronization between the medical device and a data management software on a computing device, types of peripheral devices, if any, that have been connected to the medical device and corresponding dates, times, and duration of each peripheral device connected, the application programming interfaces installed on the medical device, the frequency at which the identified peripheral devices have been used, and other such data. Although specific events are discussed, it is contemplated that the device history log may also be configured to record any and all events associated with the medical device including system notifications such as, for example, low battery indications, sensor failure, lost data packets, etc.

Referring back to FIG. 9, once the events have been stored in the device history log, the stored events are uploaded (902) to data management software stored on a personal computer or other computing device. In certain embodiments, each event stored in the device history log has a unique identifier. Therefore, each time the medical device is connected to the computing device only events that have not been previously uploaded to the computing device and/or uploaded to the device history record are uploaded. In certain embodiments, this determination is based at least in part, on the unique identifier corresponding to each event. Thus, in determining whether to upload data corresponding to a particular event, the unique identifier for the last uploaded event is compared to each unique identifier of the potentially new events to determine whether the event has already been uploaded. In certain embodiments, once the data from the device history log is stored on the computing device, the data is sent to an analysis module stored on a server for analysis. In other embodiments, the data in the device history log is uploaded directly to the analysis module stored on the server from the medical device.

In certain embodiments, the analysis module analyzes the data in the device history log to determine trends of the user. In certain embodiments, the trend data may correspond to the frequency of insulin doses, the type and brand of insulin used at various points of the day, the frequency and type of user interface screens used by the user based on detected alarm or event conditions, and the like.

After the data has been analyzed and trends identified, recommendations regarding upgrades or updates to functionalities of the medical device and/or treatment of the health condition of the user may be made (903). In certain embodiments, the recommendations may correspond to various available software upgrades for the medical device, optional applications corresponding to the treatment of the condition of the user and/or recommendations and special offers for consumable products related to the treatment of the condition of the user. For example, as discussed above, the device history log may track the software version of the medical device. Thus, when the medical device is synchronized with the data management software, the current software version of the medical device is compared against the most recent software version available. If a more recent software version for the medical device is available, the user is notified about the update.

Similarly, as discussed above, the device history log may include information to track which peripheral devices have been connected to the medical device. Based on this data, a recommendation is made to a user to download and install a particular application on the medical device. For example, if the peripheral device is pump for delivering a medication, a recommendation is made that the user should download an insulin dose calculator application.

In certain embodiments, the device history log is maintained or updated to track or update the frequency of medication doses such as insulin, the type of insulin, the brand of insulin and/or the manufacturer of the insulin. This data may be used to form recommendations for the user corresponding to various other types of insulin that may be available to the user and be comparable to the brand or type of insulin currently being used or most frequently used by the user. Further, the stored medication data may be sent to various manufacturers of the medication. In turn, the user may receive special discounts, incentives or promotions from the manufacturer for continually purchasing and/or using the particular brand of insulin. In yet other embodiments, a user may receive a recommendation for another brand of insulin from a different manufacturer including incentives, discounts and promotions for switching brands.

In certain embodiments, the device history log may be updated to track various other events that are recorded on the medical device. For example, the device history log of the medical device is updated to store various exercise events and/or meal times of the user. The device history log may also be updated based on which user interface screens are used most frequently by a user. As this data is analyzed and trends are identified, recommendations are presented to the user as to which applications the user may be interested in. For example, one application available for download from a network location may be an application configured to calculate caloric intake of various food items consumed by the user.

In certain embodiments, executable or software application recommendations may be made to the user based on previously downloaded applications. For example, one application may correspond to an insulin dose calculator application. Because the user downloaded this particular application, a user may be presented with available applications that correspond to or are related with the insulin dose calculator application on the network page. For example, the user may be presented with an alternative insulin dose calculator application or alternatively, a consumable resource tracker application configured to track amounts of insulin or test strips remaining in a user's inventory.

In certain embodiments, the available applications and incentives may be stored on a server and displayed on a webpage hosted by the server and accessible by the user. When a user identifies a particular application, incentive or the like, the user may select to download the desired application or incentive. In other embodiments, the recommendations may be sent via email, text message or other communication medium.

Figure 10:
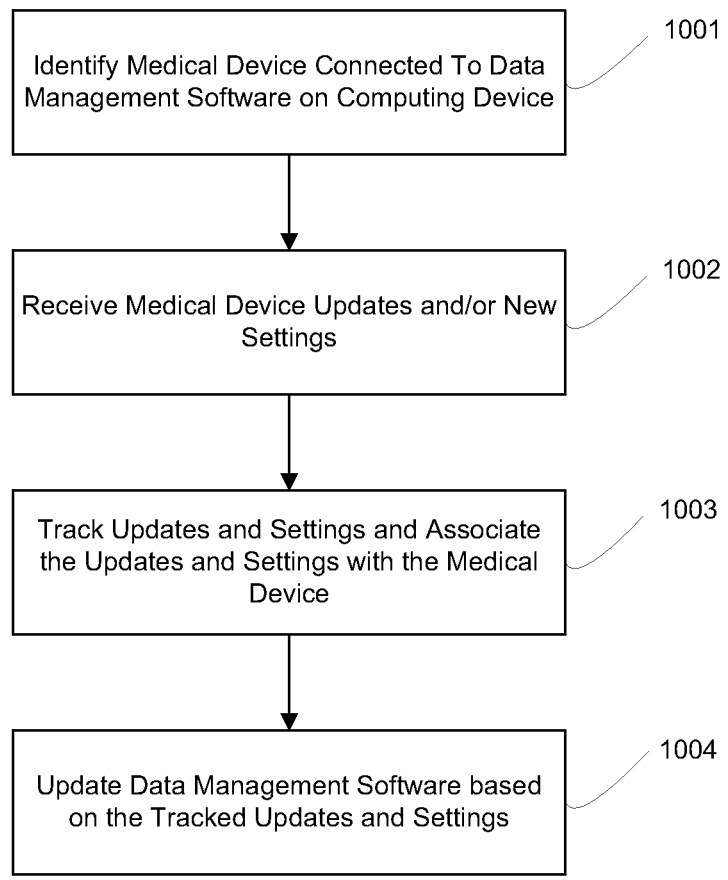
FIG. 10 is a flow chart illustrating a method for updating data management software according to embodiments of the present disclosure.

FIG. 10 illustrates a method for updating data management software according to embodiments of the present disclosure. In certain embodiments, the data management software is installed on a personal computer or other computing device and is designed to enable individuals with a health condition, such as diabetes, their care givers and/or healthcare providers to track and analyze health related data received from a medical device. In certain embodiments, the data management software allows a user to upload test data or other data from a medical device, view and print graphs and reports to assist with health management, and share data over a network with a healthcare provider. In certain embodiments, the software may also enable a healthcare provider to make updates to the medical device, change treatment plans, and/or change various settings associated with the medical device, such as, for example, minimum and maximum analyte thresholds levels, alarms and alerts associated with monitored analyte levels and the like.

To upload data from a medical device, a USB or serial cable connection or wireless connection may be used to connect the medical device to a computing device, such as a personal computer, on which the data management software is installed. Once the medical device has been connected, the data may be uploaded and stored on the computing device. In certain embodiments, data from the medical device may be wirelessly uploaded to the computing device using a Bluetooth connection or other wireless connection. If the data management software has not been installed on the computing device, the computing device downloads the data management software directly from the medical device and the data management software is installed on the computing device. Once the data management software has been installed on the computing device, data stored on the medical device may be uploaded to the computing device using a wired or wireless connection.

Referring back to FIG. 10, each time a medical device is connected to the computing device executing the data management software, the medical device is identified (1001). In certain embodiments, the medical device is identified by a serial number of the medical device, a partial serial number of the medical device or other such identifier, such as, for example, a user selected name of the medical device (e.g., "MyDevice"). When the medical device is identified, the medical device is associated with a particular user profile stored in a memory of the computing device and accessed by the data management software. As data is uploaded from the medical device to the computing device, the associated data of the user stored in the memory of the computing device is updated. If the medical device cannot be associated with a user, a new user may be added to the data management software and associated with the medical device or the medical device may be assigned to an existing user.

Referring back to FIG. 10, when the medical device has been identified, the data management software receives user initiated updates for the identified medical device and/or changes to various settings of the identified medical device (1002). In certain embodiments, the updates and settings are selected and changed from a user interface section of the data management software and propagated to the medical device. As discussed, the changes or updates may include updates to a treatment plan or updates to settings of the device such as, for example, alarm settings, times of meals, including pre-meal times and post meal times, changes to minimum and maximum threshold amounts for various analyte levels, etc. Additionally, a user may update settings directly on the medical device.

As the updates to the user's treatment plan are received and/or new settings are applied, a processor of the computing device executes the data management software to track each change made to the medical device. Additionally, the data management software may be configured to track the order in which the changes are made. In certain embodiments, the tracked data is associated with the identified medical device and/or the user associated with the identified medical device (1003). In certain embodiments, the processor of the computing device executing the data management software_analyzes the tracked data and determines what trends, if any, exist in the tracked data.

In certain embodiments, a trend is identified if a particular routine or sequence of routines is performed in substantially the same order substantially each time the identified medical device is connected to the computing device, a user is selected from a plurality of users, or when a particular user accesses the data management software. For example, trend data may indicate that each time a particular medical device (e.g., Device A) is connected to a computing device and identified by the data management software, 75% percent of the time, the user of the data management software navigates to a particular settings screen or other user interface display screen.

In other embodiments, a trend is identified if a particular routine or sequence of routines is performed in substantially the same order in response to a particular event being stored on the medical device such as, for example, an output of an alert or detection of an alarm condition (e.g., hypoglycemic alert, hypoglycemic alert etc.). For example, trend data may indicate that when an alarm or alert condition is detected and output by the medical device, or when a predetermined number of alarm or alert conditions have been detected by the medical device in a given time period, 85% of the time, a user navigates to a particular settings screen or other user interface display screen of the data management software.

Once the tracked data is analyzed and trends are identified, the data management software is upgraded based on the trend data (1004). In certain embodiments, the upgrade to the data management software may consist of placing an icon or shortcut on a home screen of the data management software that when selected, presents to the user a particular setting screen or user interface screen of the data management software. In certain embodiments, the icon or shortcut may be specific to the particular medical device that was most recently identified. Thus, each time the particular device is identified, a processor of the computing device causes the icon or shortcut to be output on the home screen of the data management software. In certain embodiments, the icon or shortcut may be specific to a particular user of the data management software. Thus, when the user logs onto the data management software, icons specific to that user are displayed. In certain embodiments, multiple patients of a healthcare provider are tracked, and various icons or shortcuts may be associated with each individual patient profile depending on the trend data identified.

Continuing with the example from above, the trend data may indicate that 75% percent of the time a user navigates to an analyte level threshold settings screen when a particular medical device is connected to the computing device. As a result, an icon or shortcut is displayed on a home screen of the data management software that directs the user directly to the analyte level threshold settings screen.

Although trend data has been described above with reference to a single setting being changed, it is contemplated that trend data may be tracked and identified for multiple setting changes or multiple sequences of events. For example, if a second particular routine or sequence of routines is performed in substantially the same order after the first particular step or sequence of steps, an icon or shortcut directing the user to a second display screen may be generated and displayed on the home page of the data management software. In certain embodiments, the second icon or shortcut may be displayed simultaneously with the first icon or shortcut. In other embodiments, the second icon or shortcut is displayed only after the first icon or shortcut has been selected. In still yet other embodiments, the second icon or shortcut may be displayed on the user interface screen that the user navigated to as a result of the user selecting the first icon or shortcut.

Additionally, although updates to treatment plans and various settings are discussed, it is contemplated that trend data may identify a particular display screen or sequence of display screens that are navigated to when a particular medical device or user is identified. For example, a healthcare provider may navigate to a first display screen showing a graph of continuous glucose levels over a predefined data range 85% of the time a particular medical device is connected to the computing device and identified by the data management software. As a result, when connection of a particular medical device to the computing device is detected, an icon or shortcut corresponding to the graph display screen is generated and placed on the home page of the data management software. If multiple display screens are accessed in a particular order, icons or shortcuts may be generated and displayed in a similar manner.

In certain embodiments, trend data and/or medical treatment plans associated with one medical device and/or a user may be compared with trend data and/or medical treatment plans from another medical device and/or user. If trend data associated with a first medical device corresponds to trend data associated with a second medical device and/or user, shortcuts or icons displayed for one user may be recommended and/or displayed when a second user is selected or when a medical device associated with the second user is identified.

In certain embodiments, a similar icon or shortcut that was displayed on a home screen of the data management software may also be displayed on a home screen of the medical device based on the trend data. Thus, a user may access a particular display screen of the medical device in response to an event in a similar manner as described above. For example, if a user navigates to a graph display screen immediately or substantially immediately after testing a blood glucose level, an icon or shortcut associated with the graph display screen is shown on the home screen of the medical device. Actuation of the icon or shortcut causes the graph display screen to be rendered on the display of the medical device.

FIG. 11 is a flow chart illustrating a method for upgrading data and/or software on a medical device and/or a computing device according to embodiments of the present disclosure. The data and/or software upgrade routine on a medical device and/or a computing device is initiated when a medical device is connected to a computing device (1101). In certain embodiments, the medical device is a health monitoring device 100 (FIG. 1), a primary receiver unit 304 (FIG. 3), or a secondary receiver unit 306 (FIG. 3) and the computing device is a personal computer, laptop, tablet computer or the like. In certain embodiments, the medical device includes a blood glucose monitor, a smart phone or personal digital assistant having glucose monitoring capabilities, or other such handheld or computing device capable of having applications or programs installed on the handheld or computing device that enables a user to track blood glucose levels or assist in the management of a disease. The connection between the medical device and the computing device may be a wireless connection or wired connection.

When the medical device is connected to the computing device, a determination is made by the computing device as to whether data management software that supports the connected medical device has been loaded onto the computing device (1102). In certain embodiments, a processor of the computing device instructs the operating system of the computing device to determine if data management software has been installed on the computing device. In certain other embodiments, the computing device may detect a device transmission identifier corresponding to the medical device. If a transmission identifier of the medical device is identified, a determination is made that the computing device is capable of communicating and interacting with the medical device.

In certain embodiments, a processor of the medical device is configured to determine if data management software has been loaded onto the computing device by checking a device history log stored on the medical device. In certain embodiments, the device history log is configured to store data corresponding to each computing device the medical device has been connected to. Such a record can include an identifier corresponding to the computing device as well as a record of what software, if any, was installed on the computing device. If data management software is installed on the computing device that supports the connected medical device, when the data management software is executed by the processor of the computing device, the processor issues instructions that causes the computing device to access a network connection, compare a version of the data management software installed on the computing device to a most current version of data management software available on the network, and/or compare a version of the medical device software installed on the medical device to a most current version of the medical device software available on the network to determine if upgrades are available (1104).

For example, when the processor of the computing device executes the data management software, and the network connection is initialized, the version of the data management software installed on the computing device is compared to the most current version of the data management software available on the network. Further, the version of the medical device software installed on the medical device is compared to a most current version of the medical device software available on the network. In certain embodiments, the comparison may be made by checking the current version of the medical device software of the medical device and/or the data management software of the computing device that is stored on the device history log to the version available on the network. In certain embodiments, the device history log also includes a record of which peripheral devices have been connected to the medical device, the current version of the software on the peripheral device, and/or a version of the API that was installed on the medical device. Thus, a determination may also be made if an upgrade is available for software corresponding to any peripheral devices that have been connected to or associated with the medical device.

If data management software is not installed on the computing device, data management software stored on the medical device is uploaded to the computing device and installed on the computing device (1103). When the newly installed data management software is executed by a processor of the computing device, the version of the data management software is compared against the most current data management software available on the network (1104). If upgrades to the data management software are not available (1105) data may be transferred from the medical device to the computing device without performing any upgrades (1106).

If an upgrade is available for the data management software being executed on the computing device, (1105), a user is presented with an option to download any and all available upgrades on a user interface screen of the data management software (1107). It is also contemplated that available upgrades for the medical device software installed on the medical device and/or upgrades for a peripheral device may also be presented to a user on a user interface of the data management software. Further, it is contemplated that upgrades may be available simultaneously for the medical device, the data management software running on the computing device, and a peripheral device. In such cases, the user may select to download one upgrade without downloading another upgrade or downloading all upgrades simultaneously or substantially simultaneously.

In cases where the user chooses to download an upgrade for the medical device software installed on the medical device, the upgrade is downloaded (1107) and stored in a memory of the medical device. In certain embodiments, the download may be stored in volatile memory or non-volatile memory of the medical device. When the download is complete, the newly downloaded software is checked for integrity (1108). In certain embodiments, the integrity of the download is verified using a cyclic redundancy check (CRC). Thus, as the data is sent from the network to the computing device, a CRC code is generated for each block of data. The CRC code is sent with the block of data and received by the medical device. When the block of data is received and/or read by a processor of the medical device, the medical device generates a CRC code for each received block of data and compares generated CRC code with the received CRC code. If the CRC codes match, the data is verified. If however, the CRC codes do not match, a data error is detected. Although a cyclic redundancy check is specifically mentioned, it is contemplated that other error detection methods may be used including using parity bits, checksums, cryptographic hash functions and the like.

If the download is verified (1109), the downloaded upgrade to the medical device software is installed on the medical device (1110). If however, it is determined that the upgrade is corrupt (e.g., an error in the downloaded code that would prevent the upgrade to the medical device software from installing or functioning properly when installed) (1109), the version of the medical device software currently being executed on the medical device is copied in the memory of the medical device over the downloaded upgrade to the medical device software (1111) to ensure the medical device has a functional backup copy of the medical device software stored in memory. In certain embodiments, a processor of the medical device may issue a command to re-download the upgrade to the medical device software and verify the upgrade to the medical device software a second time. This process may repeat for a predetermined number of times or until the download is verified by the cyclic redundancy check.

When an upgrade to the data management software installed on the computing device is available, and the user chooses to upgrade the data management software, the upgrade to the data management software is downloaded and stored directly in a memory of the medical device (1107). In certain embodiments, the downloaded upgrade to the data management software is stored in volatile memory or non-volatile memory of the medical device. When the upgrade to the data management software has been downloaded, the integrity of the download is verified (1108). In certain embodiments, the integrity of the download is verified using a cyclic redundancy check as described above.

Referring still to FIG. 11, if the integrity of the download is verified (1109) the upgrade to the data management software is uploaded from the medical device and installed on the computing device (1110). In certain embodiments, the upgrade to the data management software remains stored on the medical device even after the upgrade to the data management software has been installed on the computing device. Therefore, when the medical device is connected to a different computing device that does not have data management software installed at the time the medical device is connected, or the computing device does not have the most current data management software available, the most current data management software can be uploaded to the computing device from the medical device and installed on the computing device.

If the downloaded upgrade to the data management software is not verified, the processor of the medical device may issue an instruction causing a message screen, icon, and/or an audible notification to be output on the medical device, or the computing device, notifying the user that the download was not verified. When the user acknowledges the message screen or the icon, the user may select to download the upgrade to the data management software a second time. In certain embodiments, if the downloaded upgrade to the data management software is not verified, the processor of the medical device is configured to issue a command to restart the download. In other embodiments, the processor of the medical device may track which data packets are corrupt at the time the data packets are received and immediately or substantially immediately request that a new data packet be transmitted.

If the upgrade to the data management software that was corrupted was stored in temporary memory of the medical device, the upgrade to the data management software is overwritten by the version of the data management software that is currently being executed on the computing device to ensure the medical device has a working and verified version of the data management software stored in memory. In certain embodiments, when the upgrade to the data management software is not verified, the user may connect the medical device to a computing device with a working copy of data management software currently installed and may download the working copy of the data management software directly from the computing device.

In aspects of the present disclosure, the upgrades or updates to data and/or software discussed with respect to FIG. 11 are stored in the device history log which may be uploaded and stored in a device history record maintained by the medical device manufacturer or other entity, and/or accessible by the medical device and/or other authorized devices. The device history record may enable the manufacturer to trace, track or maintain updates or upgrades to the medical device and assist the user in troubleshooting the medical device should problems arise when upgrading the medical device. Further, although data and/or software upgrades or updates are specifically discussed with respect to FIG. 11, it is contemplated that firmware upgrades may be performed using the method described herein.

Figure 12A:
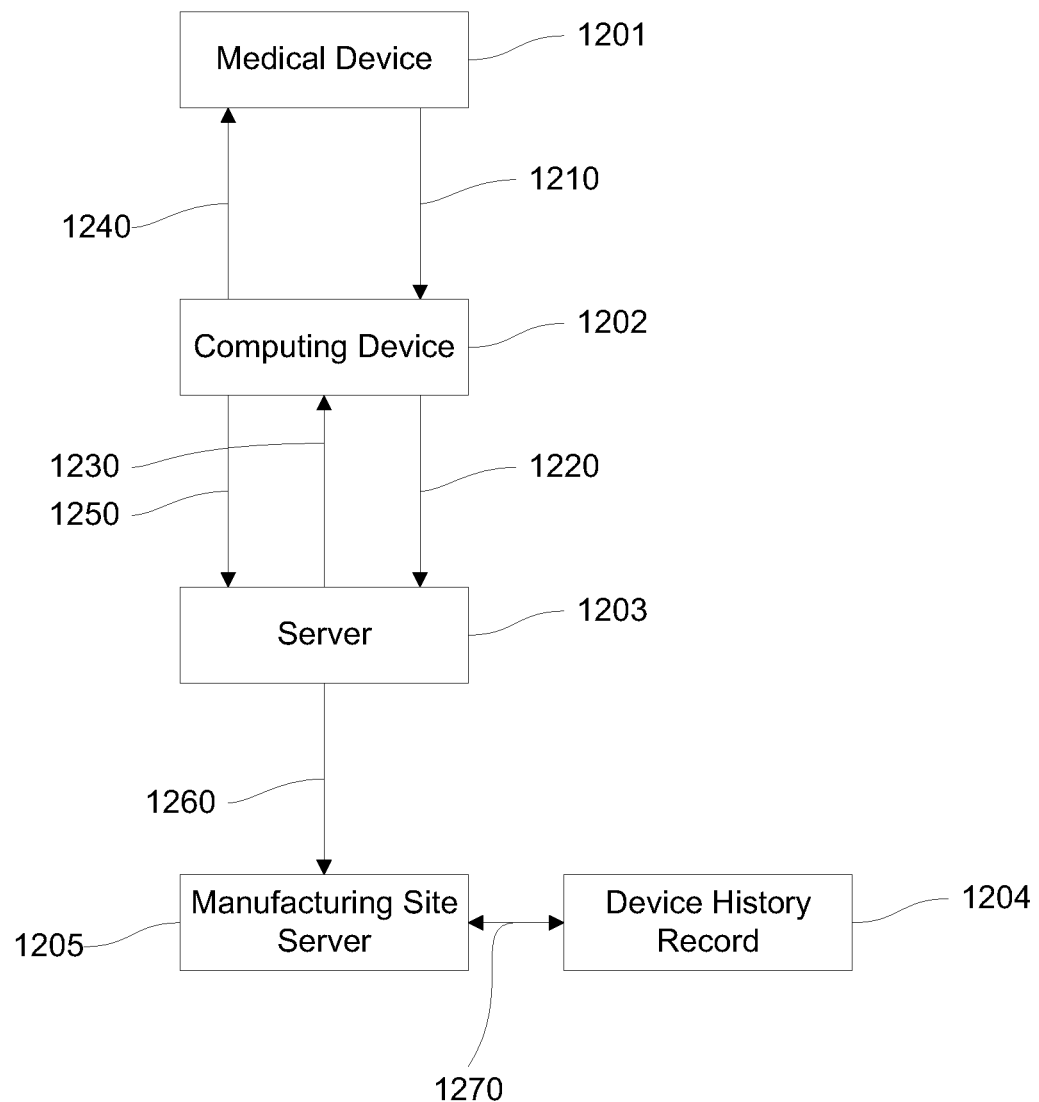
FIG. 12A is a flow chart illustrating an embodiment of a system and method for updating a device history record.

For example, in one embodiment as illustrated in FIG. 12A, a device history record for a medical device 1201 is updated each time the software or firmware or data is upgraded for that medical device 1201. For example, in one embodiment, the system and method for updating the device history record begins with connecting the medical device 1201 to a computing device 1202. The connection can be made wirelessly or wired, using any of the options disclosed herein, and the computing device 1202 can be, for example, a personal computer, a laptop computer, a notebook computer, an iPad, a tablet computer, a cell phone, a smart phone, a personal data assistant, a workstation, a server, a mainframe computer, a cloud computing system, or the like.

Once the connection is made between the medical device 1201 and computing device 1202, the medical device 1201 can send its serial number or identification number 1210 or the like to the computing device 1202. In some embodiments, the medical device 1201 can send its serial number or identification number 1210 to the computing device 1202 automatically without any prompting by the computing device 1202. In other embodiments, the medical device 1201 can send its serial number or identification number 1210 to the computing device 1202 in response to a request by the computing device 1202. Similarly, in some embodiments, the medical device 1201 can send information regarding its current software version or current firmware version or current data version to the computing device 1202, either automatically without any prompting by the computing device 1202, or in response to a request by the computing device 1202. In some embodiments, the medical device 1201 stores information regarding its serial number, identification number, current software version, current firmware version and/or current data version in a device history log, as further described above.

The computing device 1202 can check whether an upgrade is available for the software and/or firmware and/or data currently on the medical device 1201. For example, in some embodiments the computing device 1202 can send the serial number or identification number and information regarding the current software version or current firmware version or current data version 1220 of the medical device 1201 to a server 1203. In other embodiments, the computing device 1202 can send only the serial number or identification number to the server 1203, and the server 1203 can determine the software and firmware and data version on the medical device 1201 by accessing a device history record (DHR) 1204 for the medical device 1201. In other embodiments, the computing device 1202 has information regarding the latest software and firmware and data versions and based on which, for example, can determine whether an upgrade is available. For example, in some embodiments, the computing device 1202 can periodically check the server 1203 for upgrades to the software or firmware or data for the medical device 1201 even when the medical device 1201 is not connected. If upgrades are available on the server 1203, the computing device can download the data and/or software and/or firmware from the server 1203 to perform the upgrades to the data and software and firmware of the medical device 1201.

Figure 12B:
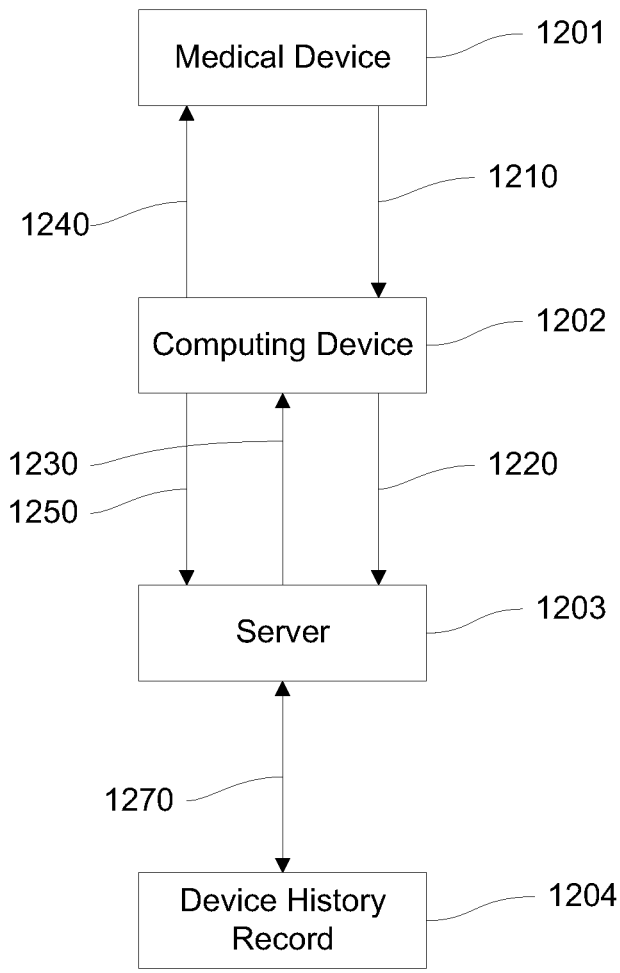
FIG. 12B is a flow chart illustrating another embodiment of a system and method for updating a device history record.

In some embodiments, the device history record 1204, as previously described herein, can contain a history of all the software and firmware and data versions that have been installed on the medical device 1201, including the currently installed software and firmware and data versions. In some embodiments, as illustrated in FIG. 12B, the device history record 1204 of the medical device 1201 can be stored on the same server 1203 that contains the data and software and firmware for upgrading the data and software and firmware on the medical device 1201. In this case, the server 1203 can request information from and update the device history record 1204 directly. In other embodiments, the device history record 1204 can be stored on a separate manufacturing site server 1205, to provide convenient storage and access for compliance with Food and Drug Administration regulations and/or inspections. In the case where the device history record 1204 is stored on a manufacturing site server 1205, the server 1203 can provide the manufacturing site server 1205 with the serial number or identification number of the medical device 1201 and request information contained in the device history record 1204 of the medical device 1201 when necessary, and also instruct the manufacturing site server 1205 to update the device history record 1204 when necessary, such as when the data or software or firmware of the medical device 1201 has been upgraded.

The server 1203 can store data and software and firmware for upgrading the data and software and firmware on the medical device 1201. The server 1203 can compare the latest data and software and firmware versions on the server 1203 with the data and software and firmware versions currently on the medical device 1201 and determine whether an upgrade is available. For example, if the latest data and/or software and/or firmware version on the server 1203 is newer than the data and/or software and/or firmware version currently on the medical device 1201, then the server 1203 can determine that an upgrade is available, and send data and software and firmware for upgrading the data and software and firmware 1230 on the medical device 1201 to the computing device 1202.

The computing device 1202 can then upgrade the data and software and firmware 1240 on the medical device 1201 using the data and software and firmware provided by the server 1203. If the upgrade is successful, the computing device 1202 can notify the server 1203 that the upgrade was successful 1250 by, for example, providing the server 1203 a message that the upgrade was successful along with the serial number or identification number for device tracking purposes and a description of the upgrades applied.

The server 1203 can instruct the manufacturing site server 1205 to update the device history record 1204 by sending a message to the manufacturing site server 1205 that the upgrade was successful 1260 along with the serial number or identification number of the medical device 1201 and a description of the upgrades applied. In response, the manufacturing site server 1205 can update the device history record 1204 to reflect that the data and/or software and/or firmware of the medical device 1201 has been upgraded 1270. In some embodiments, the updating of the device history record 1204 is automatic, as described above. In other embodiments, the device history record 1204 can be manually updated.

In some embodiments, the medical device 1201 does not function or is disabled until the medical device 1201 receives confirmation that the device history record has been updated. In this embodiment, the manufacturing site server 1205 notifies the server 1203 that the device history record 1204 has been updated, while also providing the serial number or identification number of the medical device for tracking purposes. In general, communications regarding a medical device 1201 will contain a serial number or identification number for tracking purposes. The server 1203 then notifies the computing device 1202 that the device history record 1204 has been updated, and the computing device 1201 notifies the medical device 1201 that the device history record 1204 has been updated, thereby unlocking the medical device 1201 and allowing it to function normally again.

Figure 13A:
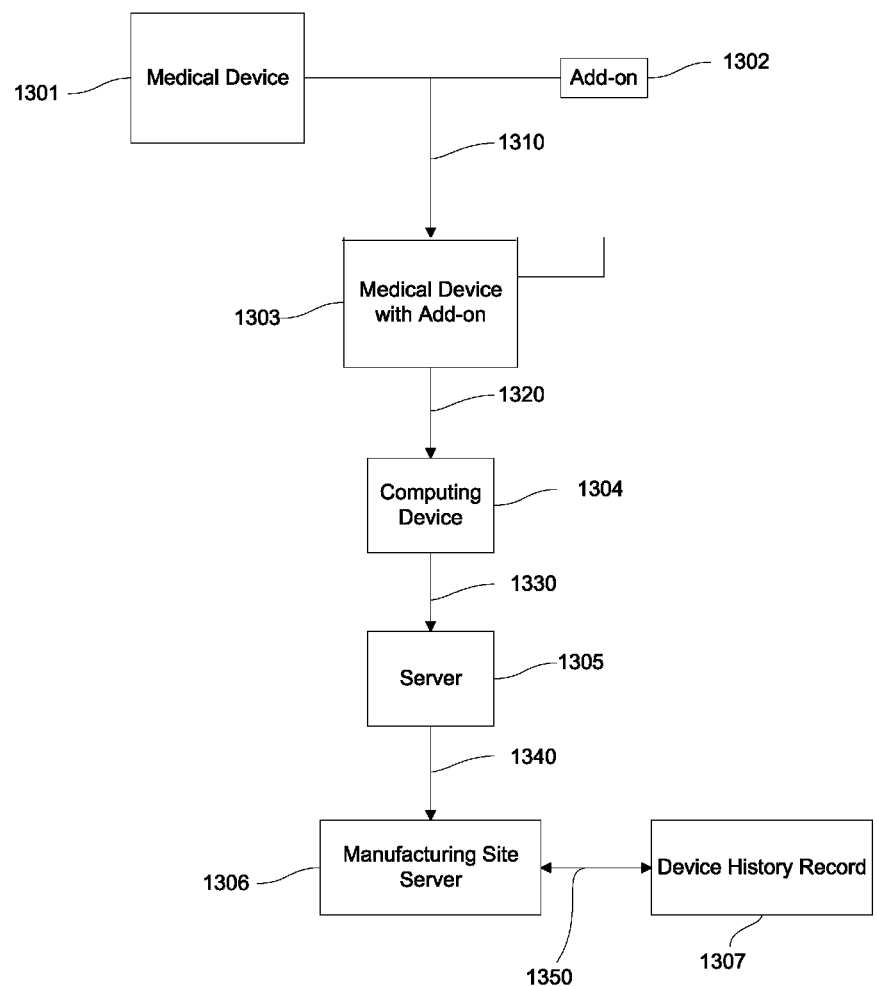
FIG. 13A is a flow chart illustrating an embodiment of a system and method for updating a device history record for a medical device combined with an add-on module.
Figure 13B:
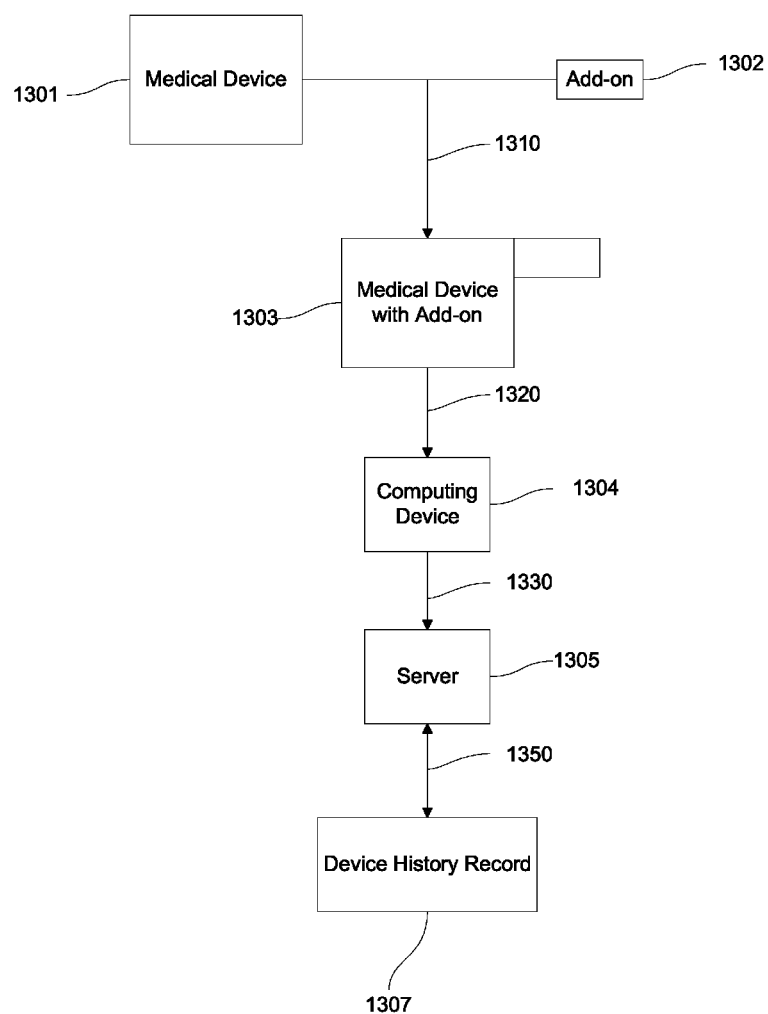
FIG. 13B is a flow chart illustrating another embodiment of a system and method for updating a device history record for a medical device combined with an add-on module.

FIGS. 13A and 13B are flow charts illustrating certain embodiments of a system and method for updating a device history record 1307 when a medical device 1301 is upgraded with a medical device add-on module 1302. When a medical device add-on module 1302 is added or combined 1310 with a medical device 1301, the medical device with add-on module 1303 can be considered a new medical device with functionality that is different from either the medical device 1301 or add-on module 1302 alone. The add-on module 1302 can be, for example, a peripheral device as described herein.

In order to update the device history record 1307 of the medical device with add-on module 1303, the medical device with add-on module 1303 can be connected 1320 to a computing device 1304. The connection can be wired or wireless, as discussed herein. The computing device 1304 can be, for example, a personal computer, a laptop computer, a notebook computer, an iPad, a tablet computer, a cell phone, a smart phone, a personal data assistant, a workstation, a server, a mainframe computer, a cloud computing system, or the like.

The medical device with add-on module 1303 can have multiple serial numbers and identification numbers, including, for example, the serial numbers and identification numbers of the medical device 1301 and add-on module 1302, as well as, in some embodiments, a unique serial number and identification number that is generated when the medical device with add-on module is formed. The medical device with add-on module 1303 can send the serial numbers and identification numbers to the computing device 1304, along with a message, in some embodiments, that the medical device 1301 and add-on module 1302 have been combined. The computing device 1304 can then send 1330 all this information, including the serial numbers and identification numbers and message, to a server 1305. The server 1305 can then send 1340 all this information, including the serial numbers and identification numbers and message, to a manufacturing site server 1306, which can update 1350 the device history record 1307 for the medical device with add-on module 1303 to indicate that the medical device 1301 has been combined with the add-on module 1302.

As illustrated in FIG. 13B, in some embodiments the server 1305 stores, accesses and modifies the device history record 1307 directly. In some embodiments, this means that the functions of the server 1305 and manufacturing site server 1306 are combined in a single server.

In some embodiments, the medical device with add-on module 1303 does not function or is disabled until it receives confirmation that the device history record 1307 has been updated. Confirmation can be passed from the manufacturing site server 1306 to the server 1305 to the computing device 1304 to the medical device with add-on module 1303, which will be activated and functional upon receipt of the confirmation.

In some embodiments, the medical device with add-on module 1303 can have its data and software and firmware updated as described herein. Depending on what upgrades are available, the data or software or firmware of either the medical device 1301 portion or the add-on module 1302 portion or both the medical device 1301 portion and the add-on module 1302 portion can be updated. In some embodiments, the medical device with add-on module 1303 has its own data and software and firmware which can be upgraded as described herein.

Figure 14:
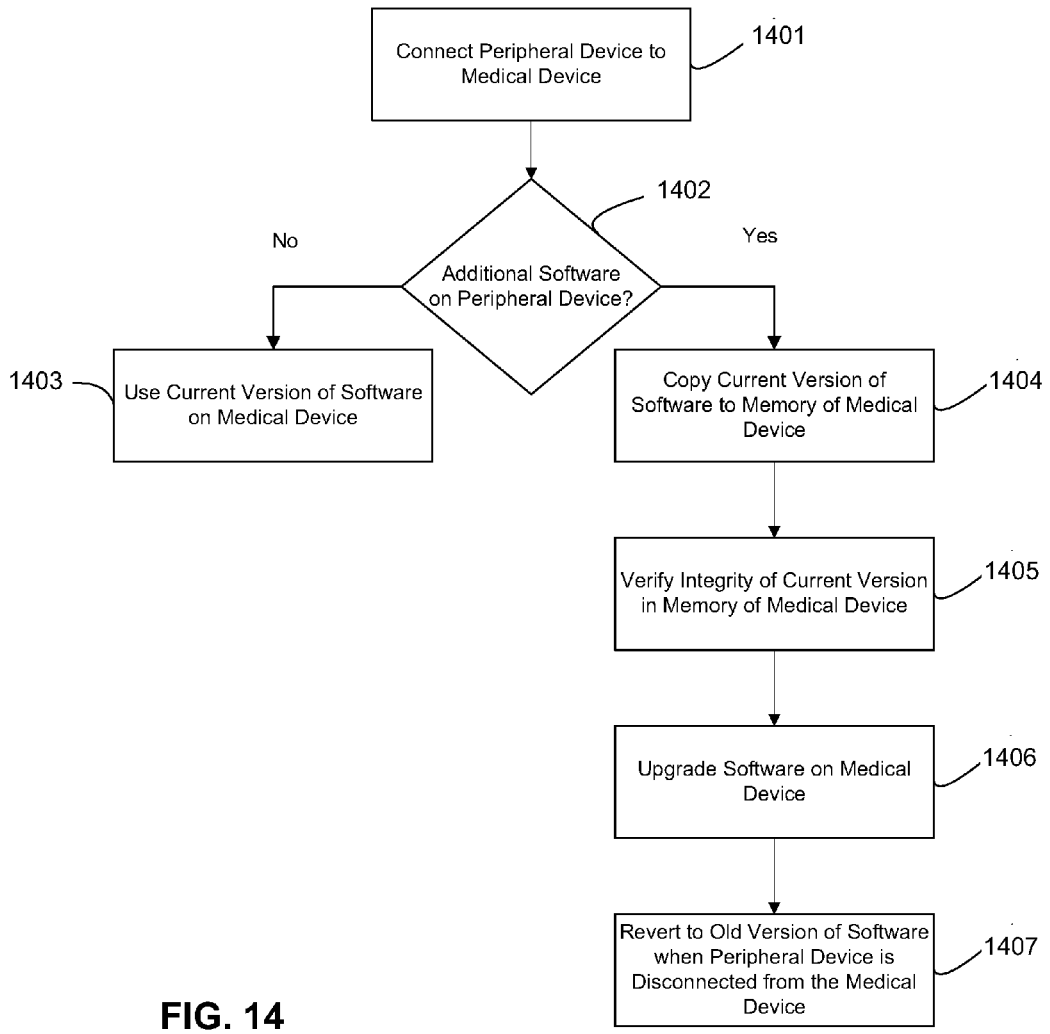
FIG. 14 is a flow chart illustrating a method for upgrading a medical device when a peripheral device is connected to the medical device according to embodiments of the present disclosure.

FIG. 14 is a flow chart illustrating a method for upgrading a medical device when a peripheral device is connected to the medical device according to embodiments of the present disclosure. The method for upgrading the medical device begins when a peripheral device is connected to the medical device (1401). In certain embodiments, the medical device is a health monitoring device 100 (FIG. 1), a primary receiver unit 304 (FIG. 3), or a secondary receiver unit 306 (FIG. 3) and the peripheral device is a test strip port, a pump for delivering fluid or another device that may be used in conjunction with the medical device. In certain embodiments, the peripheral device is a personal digital assistant, cellular telephone, tablet computer or the like. The connection between the medical device and the peripheral device may be a wireless connection, a wired connection, or the peripheral device may be physically coupled to the medical device as described above.

When the peripheral device is connected to the medical device, a processor of the medical device determines if the medical device supports the peripheral device that has been connected to the medical device and further, if data and/or software stored in a memory of the peripheral device is needed to enable the medical device to interact with the peripheral device (1402). Such a determination may be made by checking a device history log of the medical device to determine if the detected peripheral device has previously been connected to the medical device.

If identification data corresponding to an identifier of the peripheral device is stored the device history log of the medical device, a determination may be made that the peripheral device that is connected to medical device has been connected to the medical device prior to the current connection. Thus, data and/or software stored on the peripheral device may not need to be uploaded and installed on the medical device.

In certain embodiments, a processor of the medical device determines a version or type of data and/or software stored in a memory of the peripheral device. When the data and/or software stored on the peripheral device is identified, a check is performed on the medical device, using the device history log for example, to determine if the data and/or software stored on the peripheral device is loaded on the medical device. If the medical device is able to communicate and interact with the peripheral device, the data and/or software that is stored on the peripheral device is not uploaded to the medical device. As such, the data and/or software of the medical device is not upgraded (1403).

If the medical device needs a data and/or software upgraded (e.g., the data and/or software stored in the memory of the peripheral device) to interact with the peripheral device, the current version of the medical device data and/or software that is installed on medical device is copied to and stored in a memory of the medical device (1404). The current version of the data and/or software of the medical device may be stored either in non-volatile memory or in volatile memory.

When the copy of the current version of the medical device data and/or software has been stored in memory of the medical device, the integrity of the current version of the medical device data and/or software that has been transferred and stored in the memory is checked to determine if any errors exist in the current version of the data and/or software that is stored in the memory of the medical device (1405). In certain embodiments, the medical device is configured to run a cyclic redundancy check or other error detection method on the copied data and/or software. If the current version of the medical device data and/or software stored in the memory is corrupt (e.g., if there are any errors in the copied version of the medical data and/or software that would prevent the medical device data and/or software from installing and/or running on the medical device), a processor of the medical device issues an instruction for the current version of the medical device data and/or software to be copied into memory a second time to overwrite the corrupted version stored in the memory of the medical device. The integrity of the medical device data and/or software that has been copied into the memory of the medical device is again checked using a cyclic redundancy check or other error detection method. In certain embodiments, this process repeats until the integrity of the copied medical device data and/or software is verified.

When the integrity of the copied medical device data and/or software has been verified, the data and/or software stored in the memory of the peripheral device is uploaded and installed on the medical device (1406). In certain embodiments, the newly added data and/or software is an application programming interface (API) that enables the medical device to interact with data and/or software of the peripheral device. For example, if the peripheral device is a pump for dispensing medication, the API permits the medical device to act as a pump controller to control medication delivery, calculate amounts of medication to be delivered, and receive and display data corresponding to the medication delivered by the pump. In certain other embodiments, when the peripheral device is connected to the medical device, the data and/or software of the medical device is upgraded to enable the medical device to communicate with and interact with peripheral device.

When the peripheral device is disconnected from the medical device, the medical device is configured to automatically revert to the previous version of the medical device data and/or software (1407). For example, when the peripheral device is disconnected from the medical device, the processor of the medical device executes the copied medical device data and/or software stored in the memory of the medical device in place of the upgraded version of the medical device data and/or software.

Thus, the medical device is configured to run a first version of data and/or software when a peripheral device is not connected to the medical device, a second version of the data and/or software when a peripheral device is connected to the medical device, and revert back to the first version of the data and/or software when the peripheral device is removed from the medical device. In certain embodiments, the upgrade and reversion of the data and/or software occurs automatically without prompting the user and without interrupting the overall functionality of the medical device.

In certain embodiments, when the medical device is connected to a computing device as discussed above with respect to FIG. 11, and a peripheral device is connected to the medical device, the data management software installed on the computing device is upgraded in the same manner as was discussed above with respect to FIG. 11 to enable the data management software to interact with and receive data corresponding to the peripheral device. Thus, if a software upgrade for the data management software is stored on the peripheral device, the upgrade for the data management software is uploaded and stored on the medical device, and then uploaded and installed on the personal computing device.

In certain embodiments, the peripheral device can be connected directly to the computing device and a determination made if an upgrade to the data management software of the computing device is stored on the peripheral device. When the connection is established, the available data management software upgrade for the data management software is uploaded from the peripheral device and installed directly on the computing device. Additionally, the data and/or software of the peripheral device may be upgraded in a similar manner as the data and/or software of the medical device as was discussed above with respect to FIG. 11. Thus, when the peripheral device is connected to the medical device and when the combination of the peripheral device and medical device are connected to the computing device, the data management software determines if an upgrade to the data and/or software of the peripheral device is available. In certain embodiments, the determination may be made by comparing a data and/or software version of the peripheral device that is stored in the device history log with the most recent data and/or software version available on the network. If an upgrade is available, the data and/or software is downloaded, stored in a memory of the medical device and/or the peripheral device, verified, and installed on the peripheral device.

In certain embodiments, the upgrades discussed with respect to FIG. 14 are stored in the device history log and are tracked by the manufacturer as explained above. Further, although data and/or software upgrades are specifically discussed with respect to FIG. 14, it is contemplated that upgrades to firmware are accomplished using the method described above.

One aspect of the present disclosure may include detecting operable coupling of a first device with a second device, each of the first device and the second device configured to perform a corresponding first and second predetermined functions; configuring the second device coupled to the first device to operate as a third device, the third device configured to perform a third predetermined function; updating a device record corresponding to the third device based on the third predetermined function; and storing the updated device record in a memory of the third device.

In one embodiment, one or more of the first predetermined function, the second predetermined function and the third predetermined function may include one or more of blood glucose monitoring function, in vivo continuous glucose monitoring function, an in vivo glucose monitoring function, medication dosage determination function, or monitored data logging function.

In one embodiment, the first device may include an add-on module configured to physically and electrically connect to the second device.

In one embodiment, the device record may include associating a device history record with the third device.

Another aspect of the present disclosure may include detecting, using a microprocessor, an alteration or update to a medical device operation including one or more of an availability of a new firmware version executable on the medical device, a new software version executable on the medical device, a peripheral device connection, an addition of function to the medical device, or a removal of function from the medical device; updating a device history log based on the detected alteration or update to the medical device indicating the modification to the medical device; and communicating the medical device modification to a remote location including a manufacturing site of the medical device.

In one embodiment, a device history record for the medical device at the manufacturing site may be updated based on the communicated modification to the medical device.

In one embodiment, communicating the medical device modification to the remote location may include the manufacturing site of the medical device includes one or more of a wired or a wireless communication between the medical device and the remote location.

In one embodiment, the modification to the medical device may include a history of data synchronization between the medical device and other external devices or locations.

One embodiment may include storing the updated device history log in a memory of the medical device.

In one embodiment, updating the device history log is programmed to occur in real time based on the detection of the alternation or update to the medical device.

One aspect of the present disclosure may include a first device configured to perform a first predetermined function; a second device configured to perform a second predetermined function and configured to be operably coupled to the first device, the second device configured to operate as a third device configured to perform a third predetermined function when operably coupled to the first device; and a device record corresponding to the third device; wherein the device record is updated based on the third predetermined function; and wherein the updated device record is stored in a memory of the third device.

In one embodiment, one or more of the first predetermined function, the second predetermined function, and the third predetermined function includes one or more of blood glucose monitoring function, in vivo continuous glucose monitoring function, in vivo glucose monitoring function, medication dosage determination function, or monitored data logging function.

In one embodiment, the first device may include an add-on module configured to physically and electrically connect to the second device.

One embodiment may include a device history record associated with the third device.

One aspect of the present disclosure may include a medical device comprising a microprocessor; and a memory for storing instructions which, when executed by the microprocessor, causes the microprocessor to detect an alteration or update to a medical device operation including one or more of an availability of a new firmware version executable on the medical device, a new software version executable on the medical device, a peripheral device connection, an addition of function to the medical device, or a removal of function from the medical device; a device history log stored in the memory of the medical device, wherein the device history log is updated based on the detected alteration or update to the medical device indicating the modification to the medical device; and a remote location including a manufacturing site of the medical device configured to receive the medical device modification.

One embodiment may include a device history record for the medical device at the manufacturing site updated based on the received medical device modification.

One embodiment may include one or more of a wired or wireless communication link between the medical device and the remote location including the manufacturing site of the medical device.

In one embodiment, the modification to the medical device may include a history of data synchronization between the medical device and other external devices or locations.

In one embodiment, the memory for storing instruction which, when executed by the microprocessor, may cause the microprocessor to update the device history log in the memory of the medical device.

In one embodiment, the memory for storing instruction which, when executed by the microprocessor, may cause the microprocessor to update the device history log in real time based on the detection of the alternation or update to the medical device.

One aspect of the present disclosure may include establishing a connection between a peripheral device and a first medical device, the peripheral device having at least one functionality not supported by the first medical device; identifying the peripheral device; identifying data associated with the peripheral device, the identified data corresponding to the at least one functionality not supported by the first medical device; updating the first medical device based on the identified data; and controlling the at least one functionality of the peripheral device with the updated first medical device.

In one embodiment, the connection between the peripheral device and the first medical device may be a physical connection.

In another embodiment, the connection between the peripheral device and the first medical device may be a wireless connection.

In one embodiment, the peripheral device may be identified based on a serial number of the peripheral device.

In another embodiment, the peripheral device may be identified based on user selection.

In one embodiment, the identified data corresponding to the at least one functionality of the peripheral device may correspond to an application programming interface associated with the peripheral device.

In a further embodiment, the identified data corresponding to the at least one functionality of the peripheral device may be stored on the first medical device.

In another embodiment, the identified data corresponding to the at least one functionality of the peripheral device may be stored on the peripheral device.

In yet another embodiment, the identified data corresponding to the at least one functionality of the peripheral device may be stored on a computing device accessible by the first medical device.

In one embodiment, the peripheral device may be a test strip port.

In another embodiment, the peripheral device may be a pump for delivering a medication.

In another embodiment, the peripheral device may be a computing device.

In one embodiment, the first medical device may be an analyte monitoring device.

Another aspect of the present disclosure may include detecting an occurrence of a plurality of events associated with a medical device; storing the plurality of events associated with the medical device in an event log, wherein each of the plurality of events associated with the medical device has a corresponding unique identifier; transmitting at least one of the plurality of events associated with the medical device to a computing device; and receiving at least one update recommendation for the medical device, wherein the at least one update recommendation is based, at least in part, on the transmitted at least one of the plurality of events associated with the medical device.

One embodiment may further include analyzing each of the plurality of events to determine trend data associated with each of the plurality of events.

One embodiment may further include receiving update recommendations based on the trend data.

In one embodiment, the event data may correspond to a medication administered to a user.

In another embodiment, the event data may correspond to an upgrade or an update of software of the medical device.

In another embodiment, the event data may correspond to an activity of a user of the medical device.

In one embodiment, transmitting the at least one of the plurality of events associated with the medical device may comprise transmitting the at least one of the plurality of events when it has not been previously transmitted.

One embodiment may further include updating the medical device using the at least one recommendation.

In one embodiment, the medical device is an analyte monitoring device.

Another aspect of the present disclosure may include establishing a connection between a medical device and a computing device, the computing device having medical management software stored thereon; determining an identifier of the medical device; associating the medical device with a user profile associated with the medical management software, wherein the medical device is associated with the user profile based on the determined identifier of the medical device; updating at least one setting of the medical device using the medical management software; and altering a home screen of the medical management software when a frequency of an update to the at least one setting of the medical device exceeds a predetermined update frequency threshold.

In one embodiment, altering the home screen of the medical management software may comprise generating at least one icon associated with the at least one setting; and displaying the at least one icon associated with the at least one setting on the home screen of the medical management software.

One embodiment may further include rendering a display screen associated with the at least one icon when the at least one icon is selected by a user.

One embodiment may further include automatically rendering the altered home screen when a connection between the computing device and the identified medical device is established.

One embodiment may further include automatically rendering a second altered home screen associated with an identified second device when a connection between the computing device and the second identified medical device is established.

In one embodiment, the medical device may be identified based, at least in part, on a serial number.

One embodiment may further include altering a display screen of the medical device based on the altered home screen of the medical management software.

One embodiment may further include tracking a frequency of display screens accessed by a user when a connection between the medical device and the computing device is established; and altering the home screen of the medical management software when an access frequency of at least one of a plurality of display screens exceeds a predetermined access frequency threshold.

One embodiment may further include generating at least one icon associated with the at least one of the plurality of display screens; and displaying the at least one icon associated with the at least one of the plurality of display screens on the home screen of the medical management software.

One aspect of the present disclosure may include one or more processors; and a memory for storing instructions for access by the one or more processors which when executed, establishes a connection between a peripheral device and a medical device, the peripheral device having at least one functionality not supported by the medical device, identifies the peripheral device, identifies data associated with the peripheral device, the identified data corresponding to the at least one functionality not supported by the medical device, update the medical device based on the identified data, and controls the at least one functionality of the peripheral device with the updated medical device.

In one embodiment, the connection between the peripheral device and the medical device may be a physical connection.

In another embodiment, the connection between the peripheral device and the medical device may be a wireless connection.

In one embodiment, the peripheral device may be identified based on a serial number of the peripheral device.

In another embodiment, the peripheral device may be identified based on user selection.

In one embodiment, the identified data corresponding to the at least one functionality of the peripheral device may correspond to an application programming interface associated with the peripheral device.

In one embodiment, the identified data corresponding to the at least one functionality of the peripheral device may be stored on the medical device.

In another embodiment, the identified data corresponding to the at least one functionality of the peripheral device may be stored on the peripheral device.

In another embodiment, the identified data corresponding to the at least one functionality of the peripheral device may be stored on a computing device accessible by the medical device.

In one embodiment, the peripheral device may be a test strip port module.

In another embodiment, the peripheral device may be a pump for delivering a medication.

In another embodiment, the peripheral device may be a computing device.

In one embodiment, the medical device may be an analyte monitoring device.

In one embodiment, the peripheral device may be a communication device, the communication device configured to communicate with a computing device.

In one embodiment, the communication device may be configured to communicate with the computing device through a wired connection.

In one embodiment, the communication device may be configured to communicate with the computing device through a wireless connection.

In one embodiment, the computing device may include one or more of a personal computer, a laptop computer, a notebook computer, an iPad, a tablet computer, a cell phone, a smart phone, a personal data assistant, a workstation, a server, a mainframe computer and a cloud computing system.

In one embodiment, the peripheral device may be configured to receive medical data from the first medical device and medical data from a second medical device.

One embodiment may further include instructions which when executed store the medical data from the first medical device and the medical data from the second medical device in a log file.

In one embodiment, the first medical device and the second medical device may include one or more of a blood glucose meter, a continuous glucose monitoring device, an oximeter, a pulse oximeter, a temperature sensor, a respirometer, a heart rate monitor, an electrocardiogram monitor, or a blood pressure monitor.

Another aspect of the present disclosure may include one or more processors; and a memory for storing instructions for access by the one or more processors which when executed detects an occurrence of a plurality of events associated with a medical device, stores the plurality of events associated with the medical device in an event log, wherein each of the plurality of events associated with the medical device has a corresponding unique identifier, transmits at least one of the plurality of events associated with the medical device to a computing device, and receives at least one update recommendation for the medical device, wherein the at least one update recommendation is based, at least in part, on the transmitted at least one of the plurality of events associated with the medical device.

One embodiment may further include analyzing each of the plurality of events to determine trend data associated with each of the plurality of events.

One embodiment may further include receiving update recommendations based on the trend data.

In one embodiment, the event data may correspond to a medication administered to a user.

In another embodiment, the event data may correspond to an upgrade or an update of software of the medical device.

In another embodiment, the event data may correspond to an activity of a user of the medical device.

In one embodiment, transmitting the at least one of the plurality of events associated with the medical device may comprise transmitting the at least one of the plurality of events when it has not been previously transmitted.

One embodiment may further include updating the medical device using the at least one recommendation.

In one embodiment, the medical device may be an analyte monitoring device.

Another aspect of the present disclosure may include, one or more processors; and a memory for storing instructions for access by the one or more processors which when executed establishes a connection between a medical device and a computing device, the computing device having medical management software stored thereon, determines an identifier of the medical device, associates the medical device with a user profile associated with the medical management software, wherein the medical device is associated with the user profile based on the determined identifier of the medical device, updates at least one setting of the medical device using the medical management software, and alters a home screen of the medical management software when a frequency of an update to the at least one setting of the medical device exceeds a predetermined update frequency threshold.

In one embodiment, the memory for storing instructions for access by the one or more processors, which when executed may generate at least one icon associated with the at least one setting, and display the at least one icon associated with the at least one setting on the home screen of the medical management software.

In one embodiment, the memory for storing instructions for access by the one or more processors, which when executed may render a display screen associated with the at least one icon when the at least one icon is selected by a user.

In one embodiment, the memory for storing instructions for access by the one or more processors, which when executed may render the altered home screen when a connection between the computing device and the identified medical device is established.

In one embodiment, the memory for storing instructions for access by the one or more processors, which when executed may automatically render a second altered home screen associated with an identified second device when a connection between the computing device and the second identified medical device is established.

In one embodiment, the medical device may be identified, based at least in part, on a serial number.

In one embodiment, the memory for storing instructions for access by the one or more processors, which when executed may alter a display screen of the medical device based on the altered home screen of the medical management software.

In one embodiment, the memory for storing instructions for access by the one or more processors, which when executed may track a frequency of display screens accessed by a user when a connection between the medical device and the computing device is established, and alters the home screen of the medical management software when an access frequency of at least one of a plurality of display screens exceeds a predetermined access frequency threshold.

In one embodiment, the memory for storing instructions for access by the one or more processors, which when executed may generate at least one icon associated with the at least one of the plurality of display screens, and displays the at least one icon associated with the at least one of the plurality of display screens on the home screen of the medical management software.

Another aspect of the present disclosure may include establishing a connection between a peripheral device and a medical device, the peripheral device having software stored thereon for enabling communication between the peripheral device and the medical device; storing a current version of software of the medical device in a memory of the medical device; updating the software of the medical device using the software stored on the peripheral device; and reverting to the current version of the software stored in the memory of the medical device when the peripheral device is disconnected from the medical device.

One embodiment may further include verifying the integrity of the current version of the software of the medical device stored in the memory of the medical device.

One embodiment may further include copying the current version of the software of the medical device in the memory of the medical device a second time when the integrity of the current version of the software stored in the memory of the medical device is not verified.

Another aspect of the present disclosure may include one or more processors; and a memory for storing instructions for access by the one or more processors which when executed, establishes a connection between a peripheral device and a medical device, the peripheral device having software stored thereon for enabling communication between the peripheral device and the medical device, stores a current version of software of the medical device in a memory of the medical device, updates the software of the medical device using the software stored on the peripheral device, and reverts to the current version of the software stored in the memory of the medical device when the peripheral device is disconnected from the medical device.

In one embodiment, the memory for storing instructions for access by the one or more processors, which when executed may verify the integrity of the current version of the software of the medical device stored in the memory of the medical device.

In one embodiment, the memory for storing instructions for access by the one or more processors, which when executed may copy the current version of the software of the medical device in the memory a second time when the integrity of the current version of the software stored in the memory of the medical device is not verified.

Another aspect of the present disclosure may include establishing a connection between a computing device and a medical device; determining a current version of software stored on the medical device; determining whether the current version of the software stored on the medical device is the most current version of software available for the medical device; and when a more current version of software is available for the medical device: downloading the most current version of the software to the medical device; storing the most current version of the software in a memory of the medical device; checking the integrity of the most current version of the software of the medical device; installing the most current version of the software of the medical device when the integrity of the most current version of the software of the medical device is verified; and copying the current version of the software stored on the medical device over the most current version of the software of the medical device stored in the memory when the integrity of the most current version of the software of the medical device is not verified.

One embodiment may further include uploading data management software from the medical device to the computing device when data management software is not installed on the computing device.

One embodiment may further include determining if a version of the data management software installed on the computing device is a most current version of the data management software.

In one embodiment, determining a current version of software stored on the medical device may be based, at least in part, on data stored in a device history log.

Another aspect of the present disclosure may include one or more processors; and a memory for storing instructions for access by the one or more processors which when executed, establishes a connection between a computing device and a medical device, determines a current version of software stored on the medical device, determines whether the current version of the software stored on the medical device is the most current version of software available for the medical device, and when a more current version of software is available for the medical device: downloads the most current version of the software to the medical device, stores the most current version of the software in a memory of the medical device, checks the integrity of the most current version of the software of the medical device, installs the most current version of the software of the medical device when the integrity of the most current version of the software of the medical device is verified, and copies the current version of the software stored on the medical device over the most current version of the software of the medical device stored in the memory when the integrity of the most current version of the software of the medical device is not verified.

In one embodiment, the memory for storing instructions for access by the one or more processors, which when executed, may upload data management software from the medical device to the computing device when data management software is not installed on the computing device.

In one embodiment, the memory for storing instructions for access by the one or more processors, which when executed, may determine if a version of the data management software installed on the computing device is a most current version of the data management software.

In one embodiment, determining a current version of software stored on the medical device may be based, at least in part, on data stored in a device history log.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method of using a device history log of a medical device, comprising:
   running a first version of data and/or program on the medical device;
   detecting an operable coupling of the medical device with a peripheral device and receiving identification data of the peripheral device at the medical device;
   upon detecting the operable coupling, running a second version of data and/or program on the medical device, the second version being different from the first version;
   determining if the medical device is configured to support the peripheral device by comparing the identification data of the peripheral device to the device history log stored in a memory of the medical device;
   if the identification data of the peripheral device is found in the device history log, proceeding with support of the peripheral device;
   if the identification data of the peripheral device is not found in the device history log, uploading support data and/or program to the medical device to support the peripheral device, and storing identification data of the peripheral device in the medical device history log;
   determining if the operably coupled peripheral device includes a data management program;
   if the operably coupled peripheral device does not include a data management program, uploading a data management program from the medical device to the operably coupled peripheral device, the data management program having a version;
   comparing the version of the uploaded data management program from the medical device against a most current version of the data management program on a network and if a more current version exists on the network, uploading the more current version from the network to the peripheral device and running the more current version by the peripheral device.

2. The method of claim 1 further comprising the step of automatically reverting from running the second version of data and/or program to running the first version of data and/or program upon disconnection of the peripheral device from the medical device.

3. A method of updating a peripheral device configuration, comprising:
   running a first version of data and/or program on the medical device;
   detecting an operable coupling of a peripheral device to the medical device, the medical device being configured to provide medical data;
   upon detecting the operable coupling, running a second version of data and/or program on the medical device, the second version being different from the first version;
   automatically reverting from running the second version of data and/or program to running the first version of data and/or program upon disconnection of the peripheral device from the medical device;
   receiving identification data of the peripheral device in the medical device at the operable coupling;
   determining if the medical device is configured to support the peripheral device by comparing the identification data of the peripheral device to a device history log stored in a memory of the medical device;
   if the identification data of the peripheral device operably coupled to the medical device is found in the device history log, proceeding with support of the peripheral device;
   if the identification data of the peripheral device operably connected to the medical device is not found in the device history log, uploading support data and/or program to the medical device to support the peripheral device, and storing identification data of the peripheral device in the device history log;
   determining if the operably coupled peripheral device includes a data management program;
   if the operably-coupled peripheral device does not include a data management program, uploading a data management program from the operably-connected medical device to the peripheral device; and comparing a version of the uploaded data management program from the medical device against a most current version of the data management program on a network and if a more current version exists on the network, uploading the more current version from the network to the peripheral device and running the more current version by the peripheral device.

4. The method of claim 3 further comprising updating the device history log for the medical device at a manufacturing site of the medical device based on modifications to the medical device.

5. The method of claim 4 further comprising communicating modifications made to the medical device to a remote location including the manufacturing site of the medical device, the communicating including one or more of a wired or a wireless communication between the medical device and the remote location.

6. A system including a device history log, comprising:
a medical device configured to provide medical data;
a memory located in the medical device, the memory having a data management program having a version;
a medical device processor located in the medical device, the medical device processor programmed to run a first version of data and/or program on the medical device; and
a peripheral device configured to operably couple to the medical device, the peripheral device having identification data;
wherein the medical device processor is programmed to run a second version of data and/or program on the medical device upon detecting the operable coupling, the second version being different from the first version, and to communicate with the peripheral device when the medical device and peripheral device are operably coupled to determine if the peripheral device has a data management program suitable to manage the medical data provided by the medical device;
wherein the medical device processor is further programmed to automatically revert from running the second version of data and/or program to running the first version of data and/or program upon disconnection of the peripheral device from the medical device;
wherein the medical device processor is further programmed to upload the data management program from the medical device to the peripheral device if the peripheral device does not include a suitable data management program;
wherein the peripheral device is configured to run the data management program uploaded by the medical device;
wherein the medical device processor is further programmed to receive the identification data from the peripheral device and determine if the medical device is configured to support the peripheral device by comparing the identification data received from the peripheral device to a device history log stored in the medical device memory;
if the identification data of the peripheral device is found in the device history log, the medical device processor is programmed to proceed with support of the peripheral device; and
if the identification data of the peripheral device is not found in the device history log, upload support data and/or program to the medical device to support the peripheral device, and store identification data of the peripheral device in the device history log.

7. The system of claim 6 wherein the data management program uploaded by the medical device is configured to program the peripheral device to compare the version of the uploaded data management program from the medical device against a most current version of a data management program on a network and if a more current version exists on the network, to upload the more current version from the network to the peripheral device to run the more current version by the peripheral device to manage the data from the medical device.

8. A medical device system, comprising:
a medical device configured to provide medical data, comprising:
a microprocessor; and
a memory having a data management program having a version and a device history log;
a peripheral device configured to operably couple to the medical device, the peripheral device having identification data;
wherein the medical device microprocessor is programmed to run a first version of data and/or program on the medical device until the peripheral device is operably coupled to the medical device following which the medical microprocessor is programmed to run a second version of data and/or program on the medical device, the second version being different from the first version, and to automatically revert from running the second version of data and/or program to running the first version of data and/or program upon disconnection of the peripheral device from the medical device;
wherein the medical device microprocessor is further programmed to communicate with the peripheral device when the medical device and peripheral device are operably coupled to determine if the peripheral device has a data management program suitable to manage the medical data provided by the medical device;
wherein the medical device microprocessor is further programmed to upload the data management program from the medical device to the peripheral device if the peripheral device does not include a suitable data management program;
wherein the peripheral device is configured to run the data management program uploaded by the medical device;
wherein the medical device microprocessor is further programmed to receive the identification data from the peripheral device and determine if the medical device is configured to support the peripheral device by comparing the identification data received from the peripheral device to the device history log stored in the medical device memory;
if the identification data of the peripheral device is found in the device history log, the medical device processor is programmed to proceed with support of the peripheral device; and
if the identification data of the peripheral device is not found in the device history log, upload support data and/or program to the medical device to support the peripheral device and store identification data of the peripheral device in the device history log.

* * * * *